US011085050B2

(12) United States Patent
Jansens et al.

(10) Patent No.: US 11,085,050 B2
(45) Date of Patent: Aug. 10, 2021

(54) ELITE EVENT EE-GH7 AND METHODS AND KITS FOR IDENTIFYING SUCH EVENT IN BIOLOGICAL SAMPLES

(71) Applicant: BASF AGRICULTURAL SOLUTIONS SEED, US LLC, Research Triangle Park, NC (US)

(72) Inventors: Stefan Jansens, Ghent (BE); Rozemarijn Dreesen, Oostakker (BE); Wendy Aartsen, Bruges (BE); Jonas Vanhaelen, Wondelgem (BE); Hal Moser, Oceanside, CA (US); Ginger Light, Lorenzo, TX (US)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 0 days.

(21) Appl. No.: 16/095,234

(22) PCT Filed: Apr. 18, 2017

(86) PCT No.: PCT/EP2017/059096
§ 371 (c)(1),
(2) Date: Oct. 19, 2018

(87) PCT Pub. No.: WO2017/182420
PCT Pub. Date: Oct. 26, 2017

(65) Prior Publication Data
US 2019/0169632 A1    Jun. 6, 2019

Related U.S. Application Data

(60) Provisional application No. 62/324,922, filed on Apr. 20, 2016, provisional application No. 62/325,965, filed on Apr. 21, 2016.

(51) Int. Cl.
| | | |
|---|---|---|
| C12N 15/82 | (2006.01) | |
| C12Q 1/6895 | (2018.01) | |
| C12N 9/02 | (2006.01) | |
| C12N 9/10 | (2006.01) | |

(52) U.S. Cl.
CPC ....... *C12N 15/8275* (2013.01); *C12N 9/0069* (2013.01); *C12N 9/1092* (2013.01); *C12N 15/8274* (2013.01); *C12Q 1/6895* (2013.01); *C12Y 113/11027* (2013.01); *C07K 2319/08* (2013.01); *C12Q 2600/13* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,510,471 A | 4/1996 | Lebrun et al. | |
| 5,985,557 A | 11/1999 | Prudent et al. | |
| 6,001,567 A | 12/1999 | Brow et al. | |
| 6,245,968 B1 | 6/2001 | Boudec et al. | |
| 7,615,620 B2 | 11/2009 | Robinson | |
| 8,183,440 B2 * | 5/2012 | McGowen | A01H 5/12 435/421 |
| 8,592,650 B2 * | 11/2013 | Mason | C12N 15/8274 800/300 |
| 8,642,748 B2 * | 2/2014 | Mason | C12N 15/8274 536/23.2 |
| 9,062,324 B2 * | 6/2015 | Mason | A01H 5/10 |
| 9,631,202 B2 * | 4/2017 | Mason | C12N 15/8274 |
| 9,670,496 B2 * | 6/2017 | D'Halluin | C12N 9/0069 |
| 9,683,242 B2 * | 6/2017 | Mason | A01H 5/10 |
| 2002/0120964 A1 | 8/2002 | Rangwala et al. | |
| 2003/0097687 A1 | 5/2003 | Trolinder et al. | |
| 2004/0250317 A1 | 12/2004 | Huber et al. | |
| 2005/0216969 A1 | 9/2005 | Song et al. | |
| 2006/0059590 A1 | 3/2006 | Cerny et al. | |
| 2006/0130175 A1 | 6/2006 | Ellis et al. | |
| 2007/0067868 A1 | 3/2007 | Negrotto et al. | |
| 2009/0217423 A1 | 8/2009 | Cayley et al. | |
| 2010/0024077 A1 | 1/2010 | Cayley et al. | |
| 2010/0050282 A1 | 2/2010 | Trolinder et al. | |
| 2010/0077501 A1 | 3/2010 | Trolinder et al. | |

FOREIGN PATENT DOCUMENTS

| | | |
|---|---|---|
| WO | WO-97/04103 A2 | 2/1997 |
| WO | WO-02/40677 A2 | 5/2002 |
| WO | WO-2005/054480 A2 | 6/2005 |
| WO | WO-2006/128568 A2 | 12/2006 |
| WO | WO-2006/128569 A2 | 12/2006 |
| WO | WO-2006/128570 A1 | 12/2006 |
| WO | WO-2006/128572 A1 | 12/2006 |
| WO | WO-2008/151780 A1 | 12/2008 |

(Continued)

OTHER PUBLICATIONS

GenBank Locus LK596515, Sep. 22, 2014 (Year: 2014).*

(Continued)

*Primary Examiner* — Stephen Uyeno
(74) *Attorney, Agent, or Firm* — Arent Fox LLP

(57) ABSTRACT

The invention provides specific transgenic cotton plants, plant material and seeds, characterized in that these products harbor a specific herbicide tolerance transformation event at a specific location in the cotton genome. Tools are also provided which allow rapid and unequivocal identification of the event in biological samples.

20 Claims, 5 Drawing Sheets

Specification includes a Sequence Listing.

(56) References Cited

FOREIGN PATENT DOCUMENTS

| WO | WO-2012/134808 A1 | 10/2012 |
| WO | WO-2013/026740 A2 | 2/2013 |
| WO | WO-2013/112525 A2 | 8/2013 |
| WO | WO-2013/112527 A1 | 8/2013 |
| WO | WO-2013/160230 A1 | 10/2013 |
| WO | WO-2013/170398 A1 | 11/2013 |
| WO | WO-2013/170399 A1 | 11/2013 |

OTHER PUBLICATIONS

GenBank Locus AC171177, Jan. 4, 2006 (Year: 2006).*

Genbank LR699764.1 (published online Aug. 2019; see sequence in office action).*

Chaboute, et al., "Genomic organization and nucleotide sequences of two histone H3 and two histone H4 genes of *Arabidopsis thaliana*", Plant Molecular Biology, vol. 8, Issue 2, Mar. 1987, pp. 179-191.

Chaubet, et al., "Genes encoding a histone H3.3-like variant in *Arabidopsis* contain intervening sequences", Journal of Molecular Biology, vol. 225, Issue 2, May 20, 1992, pp. 569-574.

International Search Report for PCT Patent Application No. PCT/EP2017/059096, dated Jul. 7, 2017, 4 pages.

Semagn, et al., "Single nucleotide polymorphism gonotyping using Kompetitive Allele Specific PCR (KASP): overview of the technology and its application in crop improvement", Molecular Breeding, vol. 33, Issue 1, Jan. 2014, pp. 1-14.

Verdaguer, et al., "Isolation and expression in transgenic tobacco and rice plants, of the cassava vein mosaic virus (CVMV) promoter", Plant Molecular Biology, vol. 31, Issue 6, Sep. 1996, pp. 1129-1139.

Wilbur, et al., "Rapid similarity searches of nucleic acid and protein data banks", Proceedings of National Academy of Sciences of the United States of America, vol. 80, Issue 3, Feb. 1, 1983, pp. 726-730.

* cited by examiner

ELITE EVENT EE-GH7 AND METHODS AND KITS FOR IDENTIFYING SUCH EVENT IN BIOLOGICAL SAMPLES

CROSS-REFERENCE TO RELATED APPLICATIONS

This application is a 35 U.S.C. 371 National Phase of PCT Application No. PCT/EP2017/059096, filed on Apr. 18, 2017, which claims priority to US Application Nos. 62/324,922 filed Apr. 20, 2010 and 62/325,965 filed Apr. 21, 2016, the disclosures of each of which are here by incorporated by reference in their entirety.

FIELD OF THE INVENTION

This invention relates to novel nucleic acids and transgenic cotton plants, plant material and seeds, characterized by harboring a specific transformation event, particularly by the presence of genes encoding proteins that confer herbicide tolerance, at a specific location in the cotton genome. The cotton plants of the invention combine the herbicide tolerance phenotype with an agronomic performance, genetic stability and functionality in different genetic backgrounds equivalent to the corresponding non-transformed cotton genetic background in the absence of herbicide(s). This invention further provides methods and kits for identifying the presence of plant material comprising specifically transformation event EE-GH7 in biological samples.

BACKGROUND OF THE INVENTION

The phenotypic expression of a transgene in a plant is determined both by the structure of the gene or genes itself and by its or their location in the plant genome. At the same time the presence of the transgenes or "foreign DNA" at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, introgression, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary. Specific tools for use in the identification of elite event EE-GH7 in biological samples are described herein.

In this invention, EE-GH7 has been identified as an elite event from a population of transgenic cotton plants in the development of herbicide tolerant cotton (*Gossypium hirsutum*) comprising a gene coding for glyphosate tolerance combined with a gene conferring tolerance to 4-hydroxy phenylpyruvate dioxygenase (HPPD) inhibitors, each under control of a plant-expressible promoter.

Planting double-herbicide-tolerant cotton EE-GH7 varieties provides growers with new options for weed control using Isoxaflutole (IFT) and/or glyphosate herbicide. Glyphosate is widely used in cotton and other agricultural production systems. IFT herbicide offers an alternative weed control option for the cotton grower to help manage problem weed species and as an alternative mode of action tool to help slow the spread of herbicide resistant weeds. With IFT, a new mode of action is introduced in cotton that is efficacious against many weeds currently found in cotton fields.

Cotton plants comprising a herbicide tolerance gene have been disclosed in the art. WO2007/017186 describes a glyphosate tolerant elite cotton event comprising an epsps gene. WO2013/026740 describes cotton plants comprising both an hppd and an epsps gene conferring tolerance in the greenhouse and in the field. WO2013/026740 also describes cotton plants comprising both an hppd and an epsps gene which are introduced in the 3' flanking region of the elite event described in WO2008/151780 comprising an insect resistance gene. However, none of the prior art disclosures teach or suggest an elite event comprising both a gene coding for glyphosate tolerance combined with a gene conferring tolerance to HPPD inhibitors which can be used in a flexible way with or without an insect resistance gene.

It is known in the art that getting a commercial herbicide tolerant elite transformation event in cotton plants with acceptable agronomic performance, and providing sufficient herbicide tolerance, certainly to 2 different classes of herbicides, is by no means straightforward.

SUMMARY OF THE PREFERRED EMBODIMENTS OF THE INVENTION

The present invention relates to a transgenic cotton plant, or seed, cells or tissues thereof, comprising, stably integrated into its genome, an expression cassette which comprises a herbicide tolerance gene comprising the coding sequence of the 2mEPSPS gene and another herbicide tolerance gene comprising the coding sequence of the hppdPf-W336-1 Pa gene (both as described in Example 1.1 herein and as represented in SEQ ID No 1), which is tolerant to glyphosate and an HPPD inhibitor herbicide such as isoxaflutole, and, in the absence of herbicide(s), has an agronomic performance which is substantially equivalent to the non-transgenic isogenic line. After application of one or more herbicides to which tolerance is provided, the plant will have a superior agronomic phenotype compared to a non-transgenic plant.

According to the present invention the cotton plant or seed, cells or tissues thereof comprise elite event EE-GH7.

More specifically, the present invention relates to a transgenic cotton plant, seed, cells or tissues thereof, the genomic DNA of which is characterized by the fact that, when analyzed in a PCR Identification Protocol as described herein, using two primers directed to the 5' or 3' flanking region of EE-GH7 and the foreign DNA comprising herbicide tolerance genes, respectively, yields a fragment which is specific for EE-GH7. The primers may be directed against the 3' flanking region within SEQ ID NO: 1 and the foreign DNA comprising herbicide tolerance genes, respectively. The primers may also be directed against the 5' flanking region within SEQ ID NO: 1 and the foreign DNA comprising herbicide tolerance genes, respectively, such as the primers comprising or consisting (essentially) of the nucleotide sequence of SEQ ID NO: 3 and SEQ ID NO: 4, or of SEQ ID No. 5 and SEQ ID No.: 6 respectively, and yield a DNA fragment of between 50 and 1000 bp, such as a fragment of about 126 bp or of about 120 bp.

Reference seed comprising the elite event of the invention has been deposited at the ATCC under accession number PTA-122856. One embodiment of the invention is the seed comprising elite event EE-GH7 deposited as accession number PTA-122856, which will grow into a cotton plant tolerant to herbicides, particularly tolerant to glyphosate and/or HPPD inhibitors such as isoxaflutole. One embodiment of the invention is the elite event EE-GH7 as contained in seed deposited under accession number PTA-122856, which when introduced in a cotton plant will provide resistance to herbicides, particularly HPPD inhibitors such as isoxaflutole and to glyphosate. Included in this invention are minor variants of this event such as a cotton event with HPPD inhibitor tolerance and glyphosate tolerance that has a nucleotide sequence with at least 90%, at least 95%, at least 98%, at least 99%, at least 99.5%, or at least 99.9% sequence identity to the nucleotide sequence of EE-GH7 as contained in the seed deposited at the ATCC under deposit number PTA-122856, or a cotton event with HPPD inhibitor tolerance and glyphosate tolerance that has a nucleotide sequence differing in 1 to 200, 1 to 150, 1 to 100, 1 to 75, 1 to 50, 1 to 30, 1 to 20, 1 to 10, or 1 to 5 nucleotides from the nucleotide sequence of EE-GH7 as contained in the deposited seed of ATCC deposit PTA-122856, or that has a nucleotide sequence differing in 1 to 200, 1 to 150, 1 to 100, 1 to 75, 1 to 50, 1 to 30, 1 to 20, 1 to 10, or 1 to 5 nucleotides from the nucleotide sequence of SEQ ID No. 1. In one embodiment, EE-GH7 comprises a nucleotide sequence with at least 95%, at least 96%, at least 97%, at least 98%, at least 99%, at least 99.5%, or at least 99.9% sequence identity to the sequence of SEQ ID No. 1. The seed of ATCC deposit number PTA-122856, is a seed lot consisting of at least about 95% transgenic seeds homozygous for the transferred DNA, comprising the elite event of the invention, which will grow into herbicide tolerant plants, whereby the plants are glyphosate and/or isoxaflutole tolerant. The seed or progeny seed obtainable or obtained from the deposited seed (e.g., following crossing with other cotton plants with a different genetic background) can be sown and the growing plants can be treated with glyphosate or isoxaflutole as described herein to obtain 100% glyphosate or isoxaflutole tolerant plants, comprising the elite event of the invention. The invention further relates to cells, tissues, progeny, and descendants from a plant comprising the elite event of the invention grown from the seed deposited at the ATCC having accession number PTA-122856. The invention further relates to plants obtainable from (such as by propagation of and/or breeding with) a cotton plant comprising the elite event of the invention (such as a plant grown from the seed deposited at the ATCC having accession number PTA-122856). The invention also relates to cotton plants comprising elite event EE-GH7.

The invention further relates to a method for identifying a transgenic plant, or cells or tissues thereof, comprising elite event EE-GH7 which method is based on identifying the presence of characterizing DNA sequences or amino acids encoded by such DNA sequences in the transgenic plant, cells or tissues. According to a preferred embodiment of the invention, such characterizing DNA sequences are sequences of 15 bp or at least 15 bp, preferably 20 bp or at least 20 bp, most preferably 30 bp or more which comprise the insertion site of the event, i.e. both a part of the inserted foreign DNA comprising herbicide tolerance genes and a part of the cotton genome (either the 5' or 3' flanking region) contiguous therewith, allowing specific identification of the elite event. The invention also relates to plants comprising the event EE-GH7 as identified herein.

The present invention further relates to methods for identifying elite event EE-GH7 in biological samples, which methods are based on primers or probes which specifically recognize the 5' and/or 3' flanking sequence of the foreign DNA comprising the herbicide tolerance genes in EE-GH7. Any other methods to identify EE-GH7, e.g., to identify its specific characterizing sequences, are also included herein, such as whole or partial (directed) genome sequencing.

More specifically, the invention relates to a method comprising of amplifying a sequence of a nucleic acid present in biological samples, using a polymerase chain reaction with at least two primers, one of which recognizes the 5' or 3' flanking region of foreign DNA comprising the herbicide tolerance genes in EE-GH7, the other which recognizes a sequence within the foreign DNA comprising the herbicide tolerance genes, preferably to obtain a DNA fragment of between 50 and 1000 bp. The primers may recognize a sequence within the 5' flanking region of EE-GH7 (SEQ ID No. 1, from position 1 to position 1217) or within the 3' flanking region of EE-GH7 (complement of SEQ ID No 1 from position 8033 to position 9328) and a sequence within the foreign DNA comprising herbicide tolerance genes (SEQ ID No 1 from position 1218 to 8032 or the complement thereof), respectively. The primer recognizing the 5' flanking region may comprise the nucleotide sequence of SEQ ID No. 3 or SEQ ID No. 5 and the primer recognizing a sequence within the foreign DNA comprising herbicide tolerance genes may comprise the nucleotide sequence of SEQ ID No. 4 or SEQ ID No. 6 described herein. This invention also relates to the specific primers and the specific DNA amplified using such primers, as described herein.

The present invention more specifically relates to a method for identifying elite event EE-GH7 in biological samples, which method comprises amplifying a sequence of a nucleic acid present in a biological sample, using a polymerase chain reaction with two primers comprising or consisting (essentially) of the nucleotide sequence of SEQ ID No. 3 and SEQ ID No. 4 respectively, to obtain a DNA fragment of about 126 bp or with two primers comprising or consisting (essentially) of the nucleotide sequence of SEQ ID No. 5 and SEQ ID No. 6 respectively, to obtain a DNA fragment of about 120 bp. Also plants comprising the thus-identified elite event EE-GH7 are included in this invention.

The present invention further relates to the specific flanking sequences of EE-GH7 described herein, which can be used to develop specific identification methods for EE-GH7 in biological samples. Such specific flanking sequences may also be used as reference control material in identification assays. More particularly, the invention relates to the 5' and/or 3' flanking regions of EE-GH7 which can be used for the development of specific primers and probes as further described herein. Also suitable as reference material are nucleic acid molecules, preferably of about 150-850 bp, comprising the sequence which can be amplified by primers comprising or consisting (essentially) of the nucleotide sequence of SEQ ID No. 3 and SEQ ID No. 4 or of SEQ ID No. 5 and SEQ ID No. 6.

The invention further relates to identification methods for the presence of EE-GH7 in biological samples based on the use of such specific primers or probes. Primers may comprise, consist or consist essentially of a nucleotide sequence of 17 to about 200 consecutive nucleotides selected from the nucleotide sequence of SEQ ID No 1 from nucleotide 1 to nucleotide 1217 or the complement of the nucleotide sequence of SEQ ID 1 from nucleotide 8033 to nucleotide 9328, combined with primers comprising, consisting, or consisting essentially of a nucleotide sequence of 17 to about 200 consecutive nucleotides selected from the nucleotide sequence of SEQ ID No 1, such as a nucleotide sequence of 17 to about 200 consecutive nucleotides selected from the complement of the nucleotide sequence of SEQ ID No 1 from nucleotide 1218 to nucleotide 8032 or the nucleotide sequence of SEQ ID No 1 from nucleotide 1218 to nucleotide 8032. Primers may also comprise these nucleotide sequences located at their extreme 3' end, and further comprise unrelated sequences or sequences derived from the mentioned nucleotide sequences, but comprising mismatches.

The invention further relates to kits for identifying elite event EE-GH7 in biological samples, said kits comprising at least one primer or probe which specifically recognizes the 5' or 3' flanking region of the foreign DNA comprising herbicide tolerance genes in EE-GH7.

The kit of the invention may comprise, in addition to a primer which specifically recognizes the 5' or 3' flanking region of EE-GH7, a second primer which specifically recognizes a sequence within the foreign DNA comprising herbicide tolerance genes of EE-GH7, for use in a PCR Identification Protocol. The kits of the invention may comprise at least two specific primers, one of which recognizes a sequence within the 5' flanking region of EE-GH7 or a sequence within the 3' flanking region of EE-GH7, and the other which recognizes a sequence within the foreign DNA comprising herbicide tolerance genes. The primer recognizing the 5' flanking region may comprise the nucleotide sequence of SEQ ID No. 3 and the primer recognizing the transgenes or foreign DNA comprising herbicide tolerance genes may comprise the nucleotide sequence of SEQ ID No. 4, or the primer recognizing the 5' flanking region may comprise the nucleotide sequence of SEQ ID No. 5 and the primer recognizing the transgenes or foreign DNA comprising herbicide tolerance genes may comprise the nucleotide sequence of SEQ ID No. 6, or any other primer or primer combination as described herein. The kit may further comprise a probe recognizing a sequence between the primer recognizing the 5' flanking region and the primer recognizing the sequence within the foreign DNA, or recognizing a sequence between the primer recognizing the 3' flanking region and the primer recognizing the sequence within the foreign DNA, such as a probe comprising the sequence of SEQ ID No. 7.

The invention further relates to a kit for identifying elite event EE-GH7 in biological samples, said kit comprising the PCR primers comprising or consisting (essentially) of the nucleotide sequence of SEQ ID No. 3 and SEQ ID No. 4, or of the nucleotide sequence of SEQ ID No. 5 and SEQ ID No. 6 for use in the EE-GH7 PCR Identification Protocol described herein. Said kit comprising the primers comprising or consisting (essentially) of the nucleotide sequence of SEQ ID No. 5 and SEQ ID No. 6 may further comprise a probe comprising or consisting (essentially) of the nucleotide sequence of SEQ ID No. 7.

The invention also relates to a kit for identifying elite event EE-GH7 in biological samples, which kit comprises a specific probe comprising or consisting (essentially) of a sequence which corresponds (or is complementary to) a sequence having between 80% and 100% sequence identity with a specific region of EE-GH7. Preferably, the sequence of the probe corresponds to a specific region comprising part of the 5' or 3' flanking region of EE-GH7. Most preferably the specific probe comprises or consists (essentially) of (or is complementary to) a sequence having between 80% and 100% sequence identity to the sequence between nucleotide 1197 to nucleotide 1238 of SEQ ID No 1 or a sequence having between 80% and 100% sequence identity to the sequence between nucleotide 8012 to 8053 of ID No. 1.

According to another aspect of the invention, DNA sequences are disclosed comprising the insertion site of the event and sufficient length of polynucleotides of both the cotton genomic DNA and the foreign DNA comprising herbicide tolerance genes (transgene), so as to be useful as primer or probe for the detection of EE-GH7, and to characterize plants comprising event EE-GH7. Such sequences may comprise at least 9 nucleotides of the cotton genomic DNA and a similar number of nucleotides of the foreign DNA comprising the herbicide tolerance genes of EE-GH7, at each side of the junction site respectively. Most preferably, such DNA sequences comprise at least 9 nucleotides of the cotton genomic DNA and a similar number of nucleotides of the foreign DNA comprising herbicide tolerance genes contiguous with the insertion site in SEQ ID NO: 1. In one aspect of the invention, cotton plants are provided comprising such specific DNA sequences.

The methods and kits encompassed by the present invention can be used for different purposes such as, but not limited to the following: to identify the presence or determine the (lower) threshold of EE-GH7 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising EE-GH7.

The invention further relates to the 5' and/or 3' flanking regions of EE-GH7 as well as to the specific primers and probes developed from the 5' and/or 3' flanking sequences of EE-GH7.

The invention also relates to genomic DNA obtained from plants comprising elite event EE-GH7. Such genomic DNA may be used as reference control material in the identification assays herein described.

Also provided herein is a transgenic herbicide tolerant cotton plant, or cells, parts, seeds or progeny thereof, each comprising at least one elite event, said elite event comprises a foreign DNA comprising:
  i) a first chimeric gene which comprises a modified epsps gene from *Zea mays* encoding a glyphosate tolerant EPSPS enzyme under the control of a plant-expressible promoter, and
  ii) a second chimeric gene which comprises a modified hppd gene from *Pseudomonas fluorescens* encoding an HPPD inhibitor herbicide tolerant enzyme under the control of a plant-expressible promoter.

In one embodiment, said elite event comprises nucleotides 1 to 1217 of SEQ ID No 1 immediately upstream of and contiguous with said foreign DNA and nucleotides 8033 to 9328 of SEQ ID No 1 immediately downstream of and contiguous with said foreign DNA.

In a further embodiment, said elite event is obtainable by breeding with a cotton plant grown from reference seed comprising said event having been deposited at the ATCC under deposit number PTA-122856.

In another embodiment, the genomic DNA of said cotton plant, or cells, parts, seeds or progeny thereof when analyzed using the elite event identification protocol for said elite event with two primers comprising the nucleotide sequence of SEQ ID No 3 and SEQ ID No 4 respectively, yields a DNA fragment of (about) 126 bp.

Also provided herein is a method for identifying a transgenic cotton plant, or cells, parts, seed or progeny thereof tolerant to glyphosate and/or an HPPD inhibitor herbicide, such as isoxaflutole, in biological samples, said method comprising amplifying a DNA fragment of between 50 and 150 bp from a nucleic acid present in biological samples using a polymerase chain reaction with at least two primers, one of said primers recognizing the 5' flanking region of the elite event specified above, said 5' flanking region comprising the nucleotide sequence of SEQ ID No 1 from nucleotide 1 to nucleotide 1217, or the 3' flanking region of said elite event, said 3' flanking region comprising or the nucleotide sequence of the complement of SEQ ID No 1 from nucleotide 8033 to nucleotide 9328, the other primer of said primers recognizing a sequence within the foreign DNA comprising the nucleotide sequence of the complement of SEQ ID No 1 from nucleotide 1218 to nucleotide 8032 or the nucleotide sequence of SEQ ID No 1 from nucleotide 1218 to nucleotide 8032.

Also provided herein is a kit for identifying a transgenic cotton plant, or cells, parts, seed or progeny thereof tolerant to glyphosate and/or an HPPD inhibitor herbicide, such as isoxaflutole, in biological samples, said kit comprising one primer recognizing the 5' flanking region of the elite event specified above, said 5' flanking region comprising the nucleotide sequence of SEQ ID No 1 from nucleotide 1 to nucleotide 1217, or one primer recognizing the 3' flanking region of said elite event, said 3' flanking region comprising the nucleotide sequence of the complement of SEQ ID No 1 from nucleotide 8033 to nucleotide 9328, and one primer recognizing a sequence within the foreign DNA, said foreign DNA comprising the nucleotide sequence of the complement of SEQ ID No 1 from nucleotide 1218 to nucleotide 8032 or the nucleotide sequence of SEQ ID No 1 from nucleotide 1218 to nucleotide 8032.

In one embodiment of the invention, the foreign DNA of elite event EE-GH7, as used herein, comprises the nucleotide sequence of SEQ ID No 1 from nucleotide 1218 to nucleotide 8032 or its complement, or comprises a sequence with at least 95, 98, 99, or 99.5% sequence identity to the nucleotide sequence of SEQ ID No 1 from nucleotide position 1218 to nucleotide position 8032 or its complement.

Also provided herein is a cotton plant, plant cell, tissue, or seed, comprising in their genome a nucleic acid molecule comprising a nucleotide sequence with at least 97, 98, or at least 99% sequence identity to the nucleotide sequence of SEQ ID No. 1 from nucleotide position 1218 to nucleotide position 8032 or the complement thereof, or a nucleotide sequence with at least 97, 98, or at least 99% sequence identity to SEQ ID No. 1 or the complement thereof.

One embodiment of this invention provides a cotton plant, plant cell, tissue, or seed, comprising in their genome a nucleic acid molecule hybridizing to the nucleotide sequence SEQ ID No. 1 from nucleotide position 1218 to nucleotide position 8032 or the complement thereof, or hybridizing to the nucleotide sequence of SEQ ID No. 1 or the complement thereof.

Also provided herein is an isolated nucleic acid molecule comprising a nucleotide sequence with at least 99% sequence identity to the nucleotide sequence of SEQ ID No. 1 from nucleotide position 1218 to nucleotide position 8032 or the complement thereof, or a nucleotide sequence with at least 99% sequence identity to SEQ ID No. 1 or the complement thereof, or an isolated nucleic acid molecule comprising a nucleotide sequence hybridizing to the nucleotide sequence of SEQ ID No. 1 from nucleotide position 1218 to nucleotide position 8032 or the complement thereof, or hybridizing to the nucleotide sequence of SEQ ID No. 1 or the complement thereof.

Other embodiments according to the invention are summarized in the following paragraphs:

1. A nucleic acid molecule comprising a nucleotide sequence essentially similar to SEQ ID No. 1 from nucleotide 1207 to nucleotide 1228 or SEQ ID No. 1 from nucleotide 8022 to 8043, or the complement of said sequences.
2. A nucleic acid molecule comprising a nucleotide sequence essentially similar to SEQ ID No. 1 from nucleotide 1197 to nucleotide 1238 or SEQ ID No. 1 from nucleotide 8012 to 8053, or the complement of said sequences.
3. A nucleic acid molecule comprising a nucleotide sequence essentially similar to SEQ ID No. 1 or the complement of said sequence.
4. A nucleic acid molecule comprising a nucleotide sequence with at least 99% sequence identity to the nucleotide sequence of SEQ ID No. 1 or the complement thereof.
5. A nucleic acid molecule comprising a nucleotide sequence hybridizing to the nucleotide sequence of SEQ ID No. 1 or the complement thereof.
6. Cotton genomic DNA comprising the nucleic acid molecule of any one of paragraphs 1 to 5.
7. Cotton genomic DNA comprising elite event EE-GH7.
8. A chimeric DNA comprising a foreign DNA, wherein the sequence of said foreign DNA consists of the sequence of SEQ ID No. 1 from nucleotide 1218 to nucleotide 8032, flanked by a 5' and a 3' flanking region, wherein the 5' flanking region immediately upstream of and contiguous with said foreign DNA is characterized by a sequence consisting of the sequence of SEQ ID No. 1 from nucleotide 1 to nucleotide 1217, and wherein the 3' flanking region immediately downstream of and contiguous with said foreign DNA is characterized by a sequence consisting of the sequence of SEQ ID No. 1 from nucleotide 8033 to 9328.
9. The nucleic acid molecule, or genomic DNA, or chimeric DNA of any one of paragraphs 1 to 8, which is an isolated nucleic acid molecule, or an isolated genomic DNA, or an isolated chimeric DNA.
10. A cotton plant, cell, part, tissue, seed or progeny thereof, comprising the nucleic acid molecule of any one of paragraphs 1 to 5 or the chimeric DNA of paragraph 8.
11. A transgenic cotton plant, cell, part, tissue, seed or progeny thereof, each comprising elite event EE-GH7 in its genome, reference seed comprising said event having being deposited at the ATCC under deposit number PTA-122856.
12. The transgenic cotton plant, cell, part, tissue, seed or progeny thereof of paragraph 11, the genomic DNA of which, when analyzed using the Elite event identification protocol for EE-GH7 with two primers comprising the nucleotide sequence of SEQ ID 3 and SEQ ID 4 respectively, yields a DNA fragment of about 126 bp.
13. Seed comprising elite event EE-GH7 deposited at the ATCC under deposit number PTA-122856 or derivatives therefrom.
14. A cotton plant, cell, part, tissue, seed or progeny thereof comprising elite event EE-GH7 obtainable from the seed of paragraph 13.
15. A cotton plant, cell, part, tissue, seed or progeny thereof, each comprising elite event EE-GH7 in its genome, obtainable by propagation of and/or breeding with a cotton plant grown from the seed deposited at the ATCC under deposit number PTA-122856.

16. A cotton seed comprising elite event EE-GH7, reference seed comprising said event having been deposited at the ATCC under deposit number PTA-122856.
17. A transgenic cotton plant, cell, part, tissue, seed or progeny thereof, comprising elite event EE-GH7, obtainable from the seed of paragraph 16.
18. A cotton plant, cell, part, tissue, seed or progeny thereof, comprising in its genome elite event EE-GH7, wherein said elite event is the genetic locus comprising an inserted foreign DNA containing a chimeric HPPD W336 protein-encoding gene and a chimeric 2mEPSPS protein-encoding gene, and 5' and 3' flanking sequences immediately surrounding said inserted foreign DNA, as found in reference seed deposited at the ATCC under deposit number PTA-122856.
19. A transgenic cotton plant, cell, part, tissue, seed or progeny thereof, comprising in their genome event EE-GH7 characterized by a nucleic acid molecule comprising a nucleotide sequence essentially similar to SEQ ID No. 1 from nucleotide 1207 to nucleotide 1228 and a nucleic acid molecule comprising a nucleotide sequence essentially similar to SEQ ID No. 1 from nucleotide 8022 to 8043, or the complement of said sequences.
20. A cotton plant, cell, part, tissue, seed or progeny thereof, comprising EE-GH7 and comprising in the genome of its cells a nucleic acid sequence with at least 80%, 90%, 95% or 100% sequence identity to SEQ ID No. 1 from nucleotide 1197 to nucleotide 1238 and a nucleic acid sequence with at least 80%, 90%, 95% or 100% sequence identity to SEQ ID No. 1 from nucleotide 8012 to 8053, or the complement of said sequences.
21. The cotton plant according to any one of paragraphs 10 to 12, 14, 15 and 17 to 20, which is tolerant to isoxaflutole and/or glyphosate.
22. The cotton plant, cell, part, tissue, seed or progeny thereof according to any one of paragraphs 10 to 21, further comprising
    event T304-40, comprising glufosinate tolerance and the Cry1Ab gene as described in WO2008/122406;
    event GHB119 comprising glufosinate tolerance and the Cry2Ae gene as described in WO2008/151780; and/or
    event COT102 comprising the VIP3A gene as described in WO2004/039986.
23. The cotton plant cell according to any one of paragraphs 10 to 12, 14, 15 and 17 to 22, which is a non-propagating plant cell.
24. A method for producing a cotton plant or seed comprising elite event EE-GH7 comprising crossing a plant according to any one of paragraphs 10 to 12, 14, 15 and 17 to 22 with another cotton plant, and planting the seed obtained from said cross.
25. A method for producing a cotton plant tolerant to HPPD inhibitor herbicides and glyphosate, comprising introducing tolerance to HPPD inhibitor herbicides and glyphosate into the genome of a cotton plant by crossing a first cotton plant lacking an HPPD W336-encoding gene and lacking a 2mEPSPS-encoding gene with the cotton plant of any one of paragraphs 10 to 12, 14, 15 and 17 to 22, and selecting a progeny plant tolerant to HPPD inhibitor herbicides and/or glyphosate.
26. The method according to paragraph 25, wherein said progeny plant tolerant to HPPD inhibitor herbicides and/or glyphosate is selected by treating the growing plants with HPPD inhibitor herbicides and/or with glyphosate.
27. A cotton product produced from the cotton plant, cell, part, tissue, seed or progeny thereof of any one of paragraphs 10 to 22.
28. The cotton product of paragraph 27, which comprises fiber, linter, seed, seed meal or seed oil.
29. The cotton product of paragraph 27 or 28, wherein said cotton product comprises a nucleic acid that produces an amplicon diagnostic of or specific for event EE-GH7.
30. A method for producing a cotton product, comprising obtaining the cotton plant, cell, part, tissue, seed or progeny thereof of any one of paragraphs 10 to 22, and producing such cotton product therefrom.
31. The method of paragraph 30, wherein said cotton product is or comprises fiber, linter, seed, seed meal or seed oil.
32. The method of paragraph 30 or 31, wherein said cotton product comprises a nucleic acid that produces an amplicon diagnostic of or specific for event EE-GH7.
33. A method for weed control, comprising treating a field in which the cotton seeds of any one of paragraphs 10 to 22 were sown with an HPPD inhibitor herbicide, before the cotton plants emerge but after the seeds are sown.
34. A method for weed control, comprising treating the cotton plants of any one of paragraphs 10 to 12, 14, 15 and 17 to 22 with an HPPD inhibitor herbicide after the cotton plants emerged.
35. A method for protecting emerging cotton plants of any one of paragraphs 10 to 12, 14, 15 and 17 to 22 from competition by weeds, comprising treating a field to be planted with said cotton plants with an HPPD inhibitor herbicide, before the cotton plants are planted or the seeds are sown, followed by planting or sowing of said cotton plants or seeds in said pre-treated field.
36. The method according to any one of paragraphs 33 to 35, further comprising treating the cotton plants with glyphosate.
37. The process of any one of paragraph 33 to 36, wherein said HPPD inhibitor herbicide is isoxaflutole.
38. A method for weed control, comprising treating the cotton plants of any one of paragraphs 10 to 12, 14, 15 and 17 to 22 with glyphosate after the cotton plants emerged.
39. Use of the plant, seed, part, cell or progeny thereof or any one of paragraphs 10 to 22, to produce cotton fiber.
40. Use of a cotton plant or seed of any one of paragraphs 10 to 11 to grow an HPPD inhibitor herbicide-tolerant and/or glyphosate tolerant cotton plant.
41. Use of a cotton seed of any one of paragraphs 10 to 22 to obtain a cotton product, wherein said cotton product is or comprises fiber, linter, seed, seed meal or seed oil.
42. A method for identifying elite event EE-GH7 in biological samples, which method comprises detection of an EE-GH7 specific region with a specific primer pair or probe which specifically recognizes the 5' or 3' flanking region of the foreign DNA comprising herbicide tolerance genes in EE-GH7, and part of the foreign DNA contiguous with said 5' or 3' flanking region.
43. The method of paragraph 42, said method comprising amplifying a DNA fragment of between 50 and 1000 bp from a nucleic acid present in said biological samples using a polymerase chain reaction with at least two primers, wherein a first primer recognizes the 5' flanking region of the foreign DNA comprising herbicide tolerance genes in EE-GH7, said 5' flanking region comprising the nucleotide sequence of SEQ ID No. 1 from nucleotide 1 to nucleotide 1217 or wherein a first primer recognizes the 3' flanking region of the foreign DNA comprising herbicide tolerance genes in EE-GH7, said 3' flanking region comprising the nucleotide sequence of the complement of SEQ ID No. 1 from nucleotide 8033 to nucleotide 9328, and wherein a second primer recognizes a sequence within the foreign DNA comprising the nucleotide sequence of SEQ ID No. 1 from nucleotide 1218 to nucleotide 8032 or the complement thereof.

44. The method of paragraph 43, wherein said first primer recognizing the 5' flanking region comprises a nucleotide sequence of 17 to 200 consecutive nucleotides selected from the nucleotide sequence of SEQ ID No. 1 from nucleotide 1 to nucleotide 1217 or said first primer recognizing the 3' flanking region of EE-GH7 comprises a nucleotide sequence of 17 to 200 consecutive nucleotides selected from the nucleotide sequence of the complement of SEQ ID No. 1 from nucleotide 8033 to nucleotide 9328, and said second primer recognizing a sequence within the foreign DNA comprises 17 to 200 consecutive nucleotides selected from the nucleotide sequence of SEQ ID No. 1 from nucleotide 1218 to nucleotide 8032 or the complement thereof.

45. The method of paragraph 43, wherein said first primer recognizing the 5' flanking region comprises at its extreme 3' end a nucleotide sequence of at least 17 consecutive nucleotides selected from the nucleotide sequence of SEQ ID No. 1 from nucleotide 1 to nucleotide 1217 or said first primer recognizing the 3' flanking region of EE-GH7 comprises at its extreme 3' end a nucleotide sequence of at least 17 consecutive nucleotides selected from the nucleotide sequence of the complement of SEQ ID No. 1 from nucleotide 8033 to nucleotide 9328, and said second primer recognizing a sequence within the foreign DNA comprises at its 3' end at least 17 consecutive nucleotides selected from the nucleotide sequence of SEQ ID No. 1 from nucleotide 1218 to nucleotide 8032 or the complement thereof.

46. The method of paragraph 45, wherein said primers comprise the sequence of SEQ ID No. 3 and SEQ ID No. 4, respectively, or the sequence of SEQ ID No. 5 and SEQ ID No. 6, respectively, or the sequence of SEQ ID No. 11 and SEQ ID No. 13, respectively.

47. The method of paragraph 46, wherein said primers comprise at their extreme 3' end the sequence of SEQ ID No. 3 and SEQ ID No. 4, respectively, or comprise at their extreme 3' end the sequence of SEQ ID No. 5 and SEQ ID No. 6, respectively, or comprise at their extreme 3' end the sequence of SEQ ID No. 11 and SEQ ID No. 13, respectively.

48. The method of paragraph 46 or 47, wherein said primers consist of the sequence of SEQ ID No. 3 and SEQ ID No. 4, respectively, or the sequence of SEQ ID No. 5 and SEQ ID No. 6, respectively, or the sequence of SEQ ID No. 11 and SEQ ID No. 13, respectively.

49. The method of any one of paragraphs 46 to 48, which method comprises amplifying a fragment of about 126 or 120 bp using the EE-GH7 PCR Identification Protocol.

50. The method of any one of paragraphs 43 to 49, further comprising the step of hybridizing a probe specific for the DNA fragment amplified with said at least two primers.

51. The method of paragraph 50, wherein said probe recognizes part of said 5' flanking region and part of the foreign DNA contiguous therewith, or wherein said probe recognizes part of said 3' flanking region and part of the foreign DNA contiguous therewith.

52. The method of paragraph 51, wherein said primers comprise the sequence of SEQ ID No. 5 and SEQ ID No. 6, respectively, and wherein said probe comprises the sequence of SEQ ID No. 7.

53. A kit comprising a first primer recognizing the 5' flanking region of the foreign DNA comprising herbicide tolerance genes in EE-GH7, said 5' flanking region comprising the nucleotide sequence of SEQ ID No. 1 from nucleotide 1 to nucleotide 1217 or a first primer recognizing the 3' flanking region of the foreign DNA comprising herbicide tolerance genes in EE-GH7, said 3' flanking region comprising the nucleotide sequence of the complement of SEQ ID No. 2 from nucleotide 8033 to nucleotide 9328, and a second primer recognizing a sequence within the foreign DNA, said foreign DNA comprising the nucleotide sequence of SEQ ID No. 1 from nucleotide 1218 to nucleotide 8032 or the complement thereof.

54. The kit of paragraph 53, wherein said first primer recognizing the 5' flanking region comprises a nucleotide sequence of 17 to 200 consecutive nucleotides selected from the nucleotide sequence of SEQ ID No. 1 from nucleotide 1 to nucleotide 1217 or said first primer recognizing the 3' flanking region of EE-GH7 comprises a nucleotide sequence of 17 to 200 consecutive nucleotides selected from the nucleotide sequence of the complement of SEQ ID No. 1 from nucleotide 8033 to nucleotide 9328, and said second primer recognizing a sequence within the foreign DNA comprises 17 to 200 consecutive nucleotides selected from the nucleotide sequence of SEQ ID No. 1 from nucleotide 1218 to nucleotide 8032 or the complement thereof.

55. The kit of paragraph 53, wherein said first primer recognizing the 5' flanking region comprises at its extreme 3' end a nucleotide sequence of at least 17 consecutive nucleotides selected from the nucleotide sequence of SEQ ID No. 1 from nucleotide 1 to nucleotide 1217 or said first primer recognizing the 3' flanking region of EE-GH7 comprises at its extreme 3' end a nucleotide sequence of at least 17 consecutive nucleotides selected from the nucleotide sequence of the complement of SEQ ID No. 1 from nucleotide 8033 to nucleotide 9328, and said second primer recognizing a sequence within the foreign DNA comprises at its 3' end at least 17 consecutive nucleotides selected from the nucleotide sequence of SEQ ID No. 1 from nucleotide 1218 to nucleotide 8032 or the complement thereof.

56. The kit of paragraph 53, comprising a primer comprising the sequence of SEQ ID No. 3 and a primer comprising the sequence of SEQ ID No. 4 or comprising a primer comprising the sequence of SEQ ID No. 5 and a primer comprising the sequence of SEQ ID No. 6, or comprising a primer comprising the sequence of SEQ ID No. 11 and a primer comprising the sequence of SEQ ID No. 13.

57. The kit of paragraph 53, further comprising a probe recognizing a sequence between the primer recognizing the 5' flanking region and the primer recognizing the sequence within the foreign DNA, or recognizing a sequence between the primer recognizing the 3' flanking region and the primer recognizing the sequence within the foreign DNA.

58. The kit of paragraph 57, wherein said probe recognizes part of said 5' flanking region and part of the foreign DNA contiguous therewith, or wherein said probe recognizes part of said 3' flanking region and part of the foreign DNA contiguous therewith.

59. The kit of paragraph 58, wherein said primers comprise the sequence of SEQ ID No. 5 and SEQ ID No. 6, and wherein said probe comprises the sequence of SEQ ID No. 7.

60. A primer suitable for use in an EE-GH7 specific detection, comprising a sequence which, under optimized detection conditions specifically recognizes a sequence within the 5' or 3' flanking region of the foreign DNA comprising herbicide tolerance genes in EE-GH7, said 5' flanking region comprising the nucleotide sequence of SEQ ID No. 1 from nucleotide 1 to nucleotide 1217 and said 3' flanking region comprising the nucleotide sequence of the complement of SEQ ID No. 1 from nucleotide 8033 to nucleotide 9328.

61. A primer comprising at its extreme 3' end the sequence of SEQ ID No. 3, or the sequence of SEQ ID No. 5, or the sequence of SEQ ID No. 11.
62. A primer pair comprising a first primer recognizing the 5' flanking region of the foreign DNA comprising herbicide tolerance genes in EE-GH7, said 5' flanking region comprising the nucleotide sequence of SEQ ID No. 1 from nucleotide 1 to nucleotide 1217 or a first primer recognizing the 3' flanking region of the foreign DNA comprising herbicide tolerance genes in EE-GH7, said 3' flanking region comprising the nucleotide sequence of the complement of SEQ ID No. 1 from nucleotide 8033 to nucleotide 9328, and a second primer recognizing a sequence within the foreign DNA comprising the nucleotide sequence of SEQ ID No. 1 from nucleotide 1218 to nucleotide 8032 or the complement thereof.
63. A primer pair according to paragraph 62, wherein said first primer recognizing the 5' flanking region comprises a nucleotide sequence of 17 to 200 consecutive nucleotides selected from the nucleotide sequence of SEQ ID No. 1 from nucleotide 1 to nucleotide 1217 or said first primer recognizing the 3' flanking region of EE-GH7 comprises a nucleotide sequence of 17 to 200 consecutive nucleotides selected from the nucleotide sequence of the complement of SEQ ID No. 1 from nucleotide 8033 to nucleotide 9328, and said second primer recognizing a sequence within the foreign DNA comprises 17 to 200 consecutive nucleotides selected from the nucleotide sequence of SEQ ID No. 1 from nucleotide 1218 to nucleotide 8032 or the complement thereof.
64. A primer pair according to paragraph 62, wherein said first primer recognizing the 5' flanking region comprises at its extreme 3' end a nucleotide sequence of at least 17 consecutive nucleotides selected from the nucleotide sequence of SEQ ID No. 1 from nucleotide 1 to nucleotide 1217 or said first primer recognizing the 3' flanking region of EE-GH7 comprises at its extreme 3' end a nucleotide sequence of at least 17 consecutive nucleotides selected from the nucleotide sequence of the complement of SEQ ID No. 1 from nucleotide 8033 to nucleotide 9328, and said second primer recognizing a sequence within the foreign DNA comprises at its 3' end at least 17 consecutive nucleotides selected from the nucleotide sequence of SEQ ID No. 1 from nucleotide 1218 to nucleotide 8032 or the complement thereof.
65. A primer pair comprising a first primer comprising the sequence of SEQ ID No. 3 and a second primer comprising the sequence of SEQ ID No. 4, or comprising a first primer comprising the sequence of SEQ ID No. 5 and a second primer comprising the sequence of SEQ ID No. 6, or comprising a first primer comprising the sequence of SEQ ID No. 11 and a second primer comprising the sequence of SEQ ID No. 13.
66. A primer pair comprising a first primer comprising at its extreme 3' end the sequence of SEQ ID No. 3 and a second primer comprising at its extreme 3' end the sequence of SEQ ID No. 4, or comprising a first primer comprising at its extreme 3' end the sequence of SEQ ID No. 5 and a second primer comprising at its extreme 3' end the sequence of SEQ ID No. 6, or comprising a first primer comprising at its extreme 3' end the sequence of SEQ ID No. 11 and a second primer comprising at its extreme 3' end the sequence of SEQ ID No. 13.
67. A primer pair comprising a first primer consisting of the sequence of SEQ ID No. 3 and a second primer consisting of the sequence of SEQ ID No. 4, or comprising a first primer consisting of the sequence of SEQ ID No. 5 and a second primer consisting of the sequence of SEQ ID No. 6, or comprising a first primer consisting of the sequence of SEQ ID No. 11 and a second primer consisting of the sequence of SEQ ID No. 13.
68. The method of paragraph 42, which method comprises hybridizing a nucleic acid of biological samples with a specific probe for EE-GH7.
69. The method of paragraph 68, wherein the sequence of said specific probe has at least 80% sequence identity with a sequence comprising part of the 5' flanking sequence or the 3' flanking sequence of EE-GH7 and the sequence of the foreign DNA contiguous therewith.
70. The method of paragraph 69, wherein the sequence of said specific probe has at least 80% sequence identity with SEQ ID No. 1 from nucleotide 1207 to 1228 or SEQ ID No. 1 from nucleotide 8022 to 8043, or the complement of said sequences.
71. The method of paragraph 69, wherein the sequence of said specific probe has at least 80% sequence identity with SEQ ID No. 1 from nucleotide 1197 to 1238 or SEQ ID No. 1 from nucleotide 8012 to 8053, or the complement of said sequences.
72. The method of paragraph 71, wherein said probe comprises the sequence of SEQ ID No. 7.
73. A kit for identifying elite event EE-GH7 in biological samples, said kit comprising a specific probe, capable of hybridizing specifically to a specific region of EE-GH7.
74. The kit of paragraph 73, wherein the sequence of said specific probe has at least 80% sequence identity with a sequence comprising part of the 5' flanking sequence or the 3' flanking sequence of the foreign DNA comprising herbicide tolerance genes in EE-GH7 and the sequence of the foreign DNA contiguous therewith.
75. The kit of paragraph 74, wherein the sequence of said specific probe comprises a nucleotide sequence having at least 80% sequence identity with SEQ ID No. 1 from nucleotide 1197 to 1238 or SEQ ID No. 1 from nucleotide 8012 to 8053, or the complement of said sequences.
76. A specific probe for the identification of elite event EE-GH7 in biological samples.
77. The probe of paragraph 76, which comprises a nucleotide sequence having at least 80% sequence identity with a sequence comprising part of the 5' flanking sequence or the 3' flanking sequence of the foreign DNA comprising herbicide tolerance genes in EE-GH7 and the sequence of the foreign DNA contiguous therewith, or the complement thereof.
78. The probe of paragraph 77 which has at least 80% sequence identity with SEQ ID No. 1 from nucleotide 1207 to 1228 or SEQ ID No. 1 from nucleotide 8022 to 8043, or the complement of said sequences.
79. A specific probe comprising a nucleotide sequence being essentially similar to SEQ ID No. 1 from nucleotide 1197 to 1238 or SEQ ID No. 1 from nucleotide 8012 to 8053, or the complement of said sequences.
80. A specific probe consisting of the nucleotide sequence of SEQ ID No. 1 from nucleotide 1197 to 1238 or SEQ ID No. 1 from nucleotide 8012 to 8053, or the complement of said sequences.
81. A specific probe comprising the sequence of SEQ ID No. 7.
82. The primer or primer pair or probe according to any one of paragraphs 60 to 67 and 76 to 81, which comprises an unrelated nucleotide sequence at the 5' end, or which is labelled.

83. A method for confirming seed purity, which method comprises detection of an EE-GH7 specific region with a specific primer or probe which specifically recognizes the 5' or 3' flanking region of the foreign DNA comprising herbicide tolerance genes in EE-GH7, in seed samples.

84. The method of paragraph 83, comprising amplifying a DNA fragment of between 50 and 1000 bp from a nucleic acid present in said biological samples using a polymerase chain reaction with at least two primers, one of said primers recognizing the 5' flanking region of the foreign DNA comprising herbicide tolerance genes in EE-GH7, said 5' flanking region comprising the nucleotide sequence of SEQ ID No. 1 from nucleotide 1 to nucleotide 1217 or the 3' flanking region of the foreign DNA comprising herbicide tolerance genes in EE-GH7, said 3' flanking region comprising the nucleotide sequence of the complement of SEQ ID No. 1 from nucleotide 8033 to nucleotide 9328, the other primer of said primers recognizing a sequence within the foreign DNA comprising the nucleotide sequence of SEQ ID No. 1 from nucleotide 1218 to nucleotide 8032 or the complement thereof, and hybridizing a probe specific for the DNA fragment amplified with said at least two primers.

85. The method of paragraph 84, comprising amplifying a DNA fragment of 120 bp and wherein said primers comprise the sequence of SEQ ID No. 5 and SEQ ID No. 6, respectively, and wherein said probe comprises the sequence of SEQ ID No. 7.

86. A method for screening seeds for the presence of EE-GH7, which method comprises detection of an EE-GH7 specific region with a specific primer or probe which specifically recognizes the 5' or 3' flanking region of the foreign DNA comprising herbicide tolerance genes in EE-GH7, in samples of seed lots.

87. The method of paragraph 86, comprising amplifying a DNA fragment of between 50 and 1000 bp from a nucleic acid present in said biological samples using a polymerase chain reaction with at least two primers, one of said primers recognizing the 5' flanking region of the foreign DNA comprising herbicide tolerance genes in EE-GH7, said 5' flanking region comprising the nucleotide sequence of SEQ ID No. 1 from nucleotide 1 to nucleotide 1217 or the 3' flanking region of the foreign DNA comprising herbicide tolerance genes in EE-GH7, said 3' flanking region comprising the nucleotide sequence of the complement of SEQ ID No. 1 from nucleotide 8033 to nucleotide 9328, the other primer of said primers recognizing a sequence within the foreign DNA comprising the nucleotide sequence of SEQ ID No. 1 from nucleotide 1218 to nucleotide 8032 or the complement thereof, and hybridizing a probe specific for the DNA fragment amplified with said at least two primers.

88. The method of paragraph 87, comprising amplifying a DNA fragment of 120 bp and wherein said primers comprise the sequence of SEQ ID No. 5 and SEQ ID No. 6, respectively, and wherein said probe comprises the sequence of SEQ ID No. 7.

89. A method for determining the zygosity status of a plant, plant material or seed comprising elite event EE-GH7, said method comprising amplifying DNA fragments of between 50 and 1000 bp from a nucleic acid present in said biological samples using a polymerase chain reaction with at least three primers, two of said primers specifically recognizing pre-insertion plant DNA, such as a primer comprising the nucleotide sequence of SEQ ID No. 11 and a primer comprising the nucleotide sequence of SEQ ID No. 12, the third of said primers recognizing a sequence within the foreign DNA, such as the nucleotide sequence of SEQ ID No. 13.

90. A method of detecting the presence of elite event EE-GH7 in biological samples through hybridization with a substantially complementary labeled nucleic acid probe in which the probe:target nucleic acid ratio is amplified through recycling of the target nucleic acid sequence, said method comprising:
a) hybridizing said target nucleic acid sequence to a first nucleic acid oligonucleotide comprising the nucleotide sequence of SEQ ID No. 1 from nucleotide 1218 to nucleotide 1235 or its complement or said first nucleic acid oligonucleotide comprising the nucleotide sequence of SEQ ID No. 1 from nucleotide 8015 to 8032 or its complement;
b) hybridizing said target nucleic acid sequence to a second nucleic acid oligonucleotide comprising the nucleotide sequence of SEQ ID No. 1 from nucleotide 1200 to nucleotide 1217 or its complement or said labeled nucleic acid probe comprising the nucleotide sequence of SEQ ID No. 1 from nucleotide 8033 to nucleotide 8050 or its complement, wherein said first and second oligonucleotide overlap by at least one nucleotide and wherein either said first or said second oligonucleotide is labeled to be said labeled nucleic acid probe;
c) cleaving only the labeled probe within the probe:target nucleic acid sequence duplex with an enzyme which causes selective probe cleavage resulting in duplex disassociation, leaving the target sequence intact;
d) recycling of the target nucleic acid sequence by repeating steps (a) to (c); and
e) detecting cleaved labeled probe, thereby determining the presence of said target nucleic acid sequence.

BRIEF DESCRIPTION OF THE DRAWINGS

The following Examples, not intended to limit the invention to specific embodiments described, may be understood in conjunction with the accompanying Figures, incorporated herein by reference, in which.

DETAILED DESCRIPTION OF THE PREFERRED EMBODIMENTS OF THE INVENTION

Figure 1:
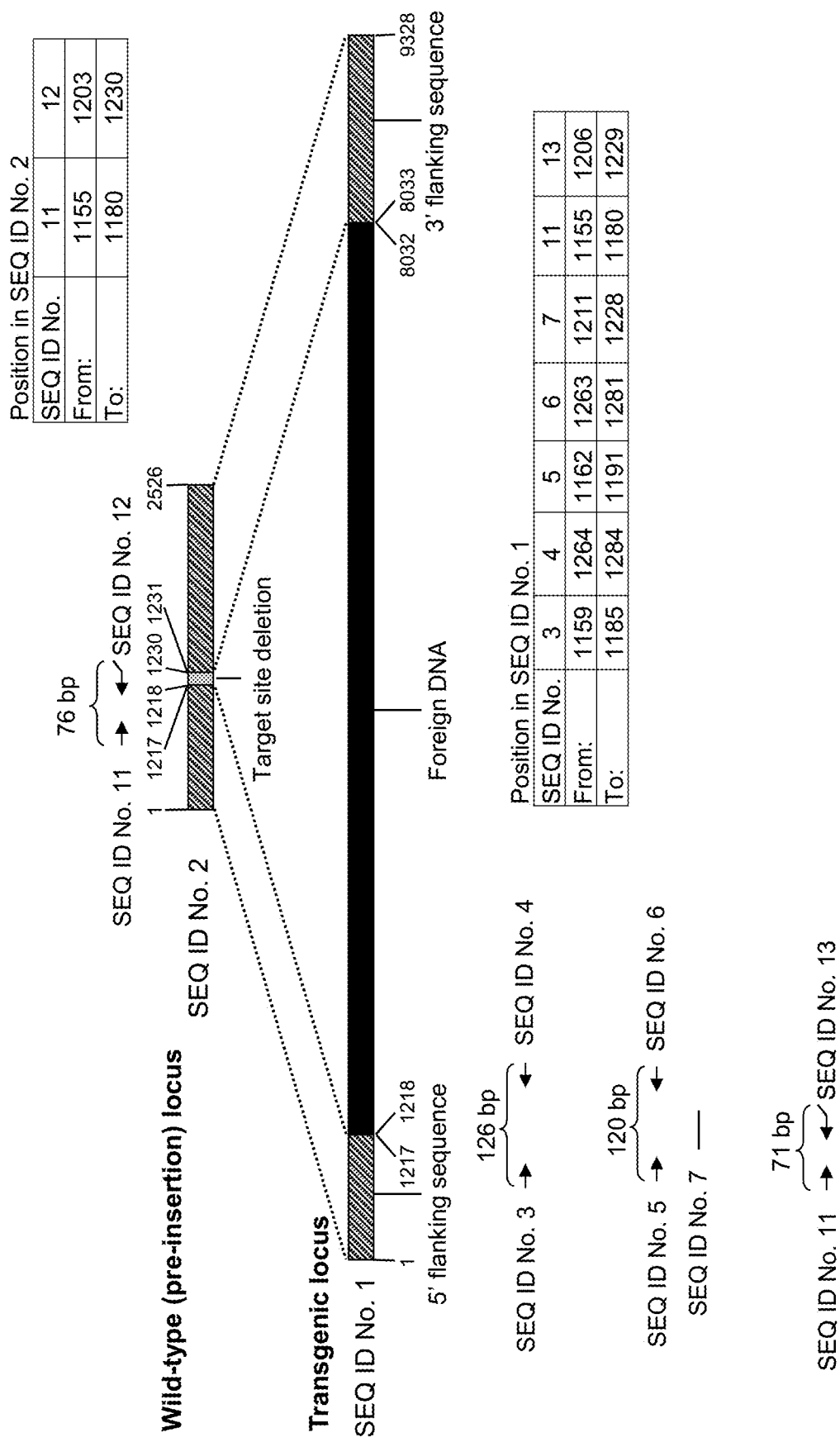
FIG. 1: Schematic representation of the relationship between the cited nucleotide sequences and primers. Black bar: foreign DNA; hatched bar: DNA of plant origin; grey bar: target site deletion. Black arrows: oligonucleotide primers, black line: oligonucleotide probe. The numbers above or below the bars representing SEQ ID No. 2 and 1 represent the nucleotide positions of the different genetic elements in said sequences. The numbers above the primer combinations indicate the length of the fragment produced in a polymerase chain reaction with these primers. The tables next to the primers represent nucleotide positions of the primers in SEQ ID No. 2 or in SEQ ID No. 1. Note: the scheme is not drawn to scale.

In this invention, EE-GH7 has been identified as an elite event from a population of transgenic cotton plants in the development of herbicide tolerant cotton (*Gossypium hirsutum*) comprising a gene coding for glyphosate tolerance combined with a gene conferring tolerance to 4-hydroxy phenylpyruvate dioxygenase (HPPD) inhibitors, each under control of a plant-expressible promoter.

The incorporation of a recombinant DNA molecule in the plant genome typically results from transformation of a cell or tissue. The particular site of incorporation is usually due to random integration.

The DNA introduced into the plant genome as a result of transformation of a plant cell or tissue with a recombinant DNA or "transforming DNA", and originating from such transforming DNA is hereinafter referred to as "foreign DNA" comprising one or more "transgenes". The transgenes of EE-GH7 are the glyphosate and HPPD inhibitor herbicide tolerance genes. "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the region of the plant genome referred to as "pre-insertion plant DNA" can be associated with a deletion of plant DNA, referred to as "target site deletion". A "flanking region" or "flanking sequence" as used herein refers to a sequence of at least 20 bp, preferably at least 50 bp, and up to 5000 bp of DNA different from the introduced DNA, preferably DNA from the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed.

An "isolated nucleic acid (sequence or molecule)" or "isolated DNA (sequence or molecule)", as used herein, refers to a nucleic acid or DNA (sequence or molecule) which is no longer in the natural environment it was isolated from, e.g., the nucleic acid sequence in another bacterial host or in a plant genome, or a nucleic acid or DNA fused to DNA or nucleic acid from another origin, such as when contained in a chimeric gene under the control of a plant-expressible promoter. Any nucleic acid or DNA of this invention, including any primer, can also be non-naturally-occurring, such as a nucleic acid or DNA with a sequence identical to a sequence occurring in nature, but having a label (missing from the naturally-occurring counterpart), or with a sequence having at least one nucleotide addition or replacement or at least one internal nucleotide deletion compared to a naturally-existing nucleotide, or with a sequence having a sequence identity below 100% (not identical) to a naturally-existing nucleic acid or DNA or a fragment thereof, or a nucleic acid or DNA with a sequence consisting of nucleotide sequences from different origins that do not occur together in nature (a chimeric or hybrid DNA), or a man-made synthetic nucleic acid or DNA with a sequence different from the natural nucleic acid or DNA or a fragment thereof.

An event is defined as a (artificial) genetic locus that, as a result of genetic engineering, carries a foreign DNA or transgene comprising at least one copy of a gene of interest or of the genes of interest. The typical allelic states of an event are the presence or absence of the foreign DNA. An event is characterized phenotypically by the expression of the transgene. At the genetic level, an event is part of the genetic make-up of a plant. At the molecular level, an event can be characterized by the restriction map (e.g., as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a population of transformants comprising a multitude of separate events, each of which is unique. An event is characterized by the foreign DNA and at least one of the flanking sequences.

An elite event, as used herein, is an event which is selected from a group of events, obtained by transformation with the same transforming DNA, based on an optimal trait efficacy and superior expression, stability of the transgene(s) and its compatibility with optimal agronomic characteristics of the plant comprising it. Thus the criteria for elite event selection are one or more, preferably two or more, advantageously all of the following:
  a) trait efficacy;
  b) that the presence of the foreign DNA does not compromise other desired characteristics of the plant, such as those relating to agronomic performance or commercial value;
  c) that the event is characterized by a well-defined molecular configuration which is stably inherited and for which appropriate tools for identity control can be developed;
  d) that the gene(s) of interest show(s) a correct, appropriate and stable spatial and temporal phenotypic expression, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two, three or all of the criteria e.g. a), b) and c) and d) above.

An "elite event" thus refers to a genetic locus comprising a foreign DNA, which meets the above-described criteria. A plant, plant material or progeny such as seeds can comprise one or more elite events in its genome.

The tools developed to identify an elite event or the plant or plant material comprising an elite event, or products which comprise plant material comprising the elite event, are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers", one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

PCR primers suitable for the invention may be the following:

oligonucleotides ranging in length from 17 nt to about 200 nt, comprising a nucleotide sequence of at least 17 consecutive nucleotides, preferably 20 consecutive nucleotides, selected from the plant DNA in the 5' flanking sequence (SEQ ID No. 1 from nucleotide 1 to nucleotide 1217) at their 3' end (primers recognizing 5' flanking sequences); or oligonucleotides ranging in length from 17 nt to about 200 nt, comprising a nucleotide sequence of at least 17 consecutive nucleotides, preferably 20 consecutive nucleotides, selected from the plant DNA in the 3' flanking sequence (complement of SEQ ID No. 1 from nucleotide 8033 to nucleotide 9328) at their 3' end (primers recognizing 3' flanking sequences); or oligonucleotides ranging in length from 17 nt to about 200 nt, comprising a nucleotide sequence of at least 17 consecutive nucleotides, preferably 20 consecutive nucleotides, selected from the inserted DNA sequences (complement of SEQ ID No. 1 from nucleotide 1218 to nucleotide 8032) at their 3' end (primers recognizing foreign DNA); or oligonucleotides ranging in length from 17 nt to about 200 nt, comprising a nucleotide sequence of at least 17 consecutive nucleotides, preferably 20 consecutive nucleotides, selected from the inserted DNA sequences (SEQ ID No. 1 from nucleotide 1218 to nucleotide 8032) at their 3' end (primers recognizing foreign DNA); or suitable oligonucleotides ranging in length from 17 nt to about 200 nt, comprising a nucleotide sequence of at least 17 consecutive nucleotides, preferably 20 consecutive nucleotides, selected from the nucleotide sequence of the inserted DNA fragment or its complement (SEQ ID No. 1 from nucleotide 1218 to nucleotide 8032).

It will be understood that primers recognizing the 5' flanking sequences can be used in a PCR reaction together with primers recognizing the foreign DNA which are selected from the complement of SEQ ID No. 1 from nucleotide 1218 to nucleotide 8032, whereas primers recognizing the 3' flanking sequences can be used in a PCR reaction together with primers recognizing the foreign DNA which are selected from directed to SEQ ID No. 1 from nucleotide 1218 to nucleotide 8032.

The primers may of course be longer than the mentioned 17 consecutive nucleotides, and may, e.g., be 20, 21, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may comprise or consist of a nucleotide sequence selected from the flanking sequences or foreign DNA, as appropriate, but may contain several (e.g., 1, 2, 5, or 10) mismatches. The 5' sequence of the primers may even entirely be a nucleotide sequence unrelated to the flanking sequences or foreign DNA, such as, e.g., a nucleotide sequence representing one or more restriction enzyme recognition sites, or such as nucleotide sequences capable of binding other oligonucleotides, such as labelled oligonucleotides, such as FRET cassettes (LGC genomics; see Semagn et al., 2014, Mol Breeding 33:1-14, and U.S. Pat. No. 7,615,620). Such unrelated sequences or flanking DNA sequences with mismatches should preferably not be longer than 100, more preferably not longer than 50 or even 25 nucleotides. The primers can also be modified with a label, such as a fluorescent label.

Moreover, suitable primers may comprise or consist (essentially) of a nucleotide sequence at their 3' end spanning the joining region between the plant DNA derived sequences and the foreign DNA sequences (located at nucleotides 1217 and 1218 in SEQ ID No 1 and nucleotides 8032 and 8033 in SEQ ID No 1) provided the mentioned 3'-located 17 consecutive nucleotides are not derived exclusively from either the foreign DNA or plant-derived sequences in SEQ ID No. 1.

It will also be immediately clear to the skilled artisan that properly selected PCR primer pairs should also not comprise sequences complementary to each other.

Primers and probes according to the invention can be labelled, such as, for example, with fluorescent labels or quenchers as described elsewhere herein.

Primers according to the invention can have unrelated sequences at the 5' end. Probes according to the invention can have unrelated sequences at the 5' end and/or at the 3' end. Such unrelated sequences can, for example, be sequences that are designed to bind to secondary primers, or can be sequences comprising restriction sites, or can be any unrelated sequences.

For the purpose of the invention, the "complement of a nucleotide sequence represented in SEQ ID No: X" is the nucleotide sequence which can be derived from the represented nucleotide sequence by replacing the nucleotides with their complementary nucleotide according to Chargaff's rules (A⇔T; G⇔C) and reading the sequence in the 5' to 3' direction, i.e., in opposite direction of the represented nucleotide sequence.

Examples of suitable primers are the oligonucleotide sequences of SEQ ID No 3, SEQ ID no. 5 or SEQ ID No. 11 (5' flanking sequence recognizing primer), or SEQ ID No 4, SEQ ID No. 6 (foreign DNA recognizing primer for use with the 5' flanking sequence recognizing primers).

Preferably, the amplified fragment has a length of between 50 and 500 nucleotides, such as a length between 50 and 150 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

Detection of integration fragments can occur in various ways, e.g., via size estimation after gel analysis. The integration fragments may also be directly sequenced. Other sequence specific methods for detection of amplified DNA fragments are also known in the art. Amplified DNA fragments can also be detected using labelled sequences and detection of the label. For example, a labelled probe can be included in the reaction mixture which specifically binds to the amplified fragment. The labelled probe (FRET hybridization probe) can comprise a fluorescent label and a quencher, such that FRET cassette is no longer quenched and emits fluorescence when bound to the PCR product. Alternatively, a labelled FRET cassette, i.e. an oligonucleotide labelled with a fluorescent label and a quencher, can be included in the reaction mixture which specifically binds one of the primers in the reaction mixture, such as a FRET cassette directed to a 5' extension of the primer used in the reaction mixture (see, e.g., see Semagn et al., 2014, Mol Breeding 33:1-14, and U.S. Pat. No. 7,615,620). Fluorescence can be measured using methods known in the art. Fluorescence can be measured real-time, i.e. during each cycle of the PCR reaction. Fluorescence can also be measured at the end of the PCR reaction.

As the sequence of the primers and their relative location in the genome are unique for the elite event, amplification of the integration fragment will occur only in biological samples comprising (the nucleic acid of) the elite event. Preferably when performing a PCR to identify the presence of EE-GH7 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in "PCR Applications Manual" (Roche Molecular Biochemicals, 2nd Edition, 1999) and other references. The optimal conditions for the PCR, including the sequence of the specific primers, are specified in a "PCR (or Polymerase Chain Reaction) Identification Protocol" for each elite event. It is however understood that a number of parameters in the PCR Identification Protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR Identification Protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying EE-GH7 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g., via labeling of the nucleic acid or probe), whereby the formation of this hybrid indicates the presence of EE-GH7. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

Oligonucleotides suitable as PCR primers for detection of the elite event EE-GH7 can also be used to develop a PCR-based protocol to determine the zygosity status of plants containing the elite event. To this end, two primers recognizing the wild-type locus before integration are designed in such a way that they are directed towards each other and have the insertion site located in between the primers. These primers may be primers specifically recognizing the 5' and 3' flanking sequences contained within SEQ ID No. 1. These primers may also be primers specifically recognizing the 5' or 3' flanking sequence. This set of primers, together with a third primer complementary to transforming DNA sequences (foreign DNA) allows simultaneous diagnostic PCR amplification of the EE-GH7 specific locus, as well as of the wild type locus. If the plant is homozygous for the transgenic locus or the corresponding wild type locus, the diagnostic PCR will give rise to a single PCR product typical, preferably typical in length, for either the transgenic or wild type locus. If the plant is hemizygous for the transgenic locus, two locus-specific PCR products will appear, reflecting both the amplification of the transgenic and wild type locus.

Alternatively, to determine the zygosity status of plants containing the elite event, two primers recognizing the wild-type locus before integration are designed in such a way that they are directed towards each other, and that one primer specifically recognizes the 5' or the 3' flanking sequences contained within SEQ ID No. 1, and that one primer specifically recognizes the 3' or the 5' flanking sequences contained within SEQ ID No. 1, or specifically recognizes the target site deletion. For the current invention, particularly suitable primers recognizing the wild type locus before integration are primers comprising or consisting (essentially) of the nucleotide sequence of SEQ ID No 11 and SEQ ID No. 12. This set of primers, together with a third primer complementary to transforming DNA sequences (foreign DNA), or complementary to transforming DNA sequences and the 5' or 3' flanking sequences contiguous therewith, and in a direction towards the primer which specifically recognizes the 5' or the 3' flanking sequences (such as a primer comprising or consisting (essentially) of the nucleotide sequence of SEQ ID No 13, which is in a direction towards the primer comprising or consisting (essentially) of the nucleotide sequence of SEQ ID No 11) allow simultaneous diagnostic PCR amplification of the EE-GH7 specific locus, as well as of the wild type locus. If the plant is homozygous for the transgenic locus or the corresponding wild type locus, the diagnostic PCR will give rise to a single PCR product typical for either the transgenic or wild type locus. If the plant is hemizygous for the transgenic locus, two locus-specific PCR products will appear, reflecting both the amplification of the transgenic and wild type locus.

Detection of the PCR products typical for the wild-type and transgenic locus can be based on determination of the length of the PCR products which can be typical for the wild-type and transgenic locus. Alternatively, detection of the PCR products typical for the wild-type and transgenic locus can be performed by modification of the primer specific for the target site deletion and by modification of the primer specific for the foreign DNA, and detection of incorporation into a PCR product of the modified primers. For example, the primer specific for the target site deletion and the primer specific for the foreign DNA can be labelled using a fluorescent label, wherein the labels are different for the two primers. Fluorescence can be detected when the primer is incorporated into a PCR product. If the plant is homozygous for the transgenic locus or the corresponding wild type locus, fluorescence can be detected of the label of the primer specific for the foreign DNA only or of the primer specific for the target site deletion only. If the plant is hemizygous for the transgenic locus, fluorescence can be detected of both the label of the primer specific for the foreign DNA and of the primer specific for the target site deletion, reflecting both the amplification of the transgenic and wild type locus.

Alternatively, the primer specific for the target site deletion and the primer specific for the foreign DNA can have a 5' extension which specifically bind a labelled FRET cassette, i.e. an oligonucleotide labelled with a fluorescent label and a quencher, wherein the 5' extension and the corresponding FRET cassettes are different for the two primers (see, e.g., see Semagn et al., 2014, Mol Breeding 33:1-14, and U.S. Pat. No. 7,615,620). Fluorescence can be detected when the primer is incorporated into a PCR product and, subsequently, the FRET cassette is incorporated in the PCR product. If the plant is homozygous for the transgenic locus or the corresponding wild type locus, fluorescence can be detected of the FRET cassette specifically binding to the primer specific for the foreign DNA only or of the FRET cassette specifically binding to the primer specific for the target site deletion only. If the plant is hemizygous for the transgenic locus, fluorescence can be detected of both of the FRET cassette specifically binding to the primer specific for the foreign DNA and of the FRET cassette specifically binding to the primer specific for the target site deletion, reflecting both the amplification of the transgenic and wild type locus.

If the plant is homozygous for the transgenic locus or the corresponding wild type locus, the diagnostic PCR will give rise to a single PCR product typical, preferably typical in length, for either the transgenic or wild type locus. If the plant is hemizygous for the transgenic locus, two locus-specific PCR products will appear, reflecting both the amplification of the transgenic and wild type locus.

Alternatively, to determine the zygosity status of plants containing the elite event, presence of the event can be determined in a PCR reaction in a quantitative way as described in Example 2.2.2. To this end, two primers recognizing the transgenic are designed in such a way that they are directed towards each other, wherein one primer specifically recognizes the 5' or 3' flanking sequence contained within SEQ ID No. 1, (such as a primer comprising or consisting (essentially) of the nucleotide sequence of SEQ ID No 5) and wherein one primer specifically recognizes the foreign DNA within SEQ ID no. 1 (such as a primer comprising or consisting (essentially) of the nucleotide sequence of SEQ ID No 6). This set of primers allows PCR amplification of the EE-GH7 specific locus. The amplified DNA fragment can quantitatively be detected using a labelled probe which is included in the reaction mixture which specifically binds to the amplified fragment (such as a probe comprising or consisting (essentially) of the nucleotide sequence of SEQ ID No 7). The labelled probe (FRET hybridization probe) can comprise a fluorescent label and a quencher, such that FRET cassette is no longer quenched and emits fluorescence when bound to the PCR product. Fluorescence can be measured real-time, i.e. during each cycle of the PCR reaction, using methods known in the art. The PCR cycle at which the fluorescence exceeds a certain threshold level is a measure for the amount of EE-GH7 specific locus in the biological sample which is analyzed, and the zygosity status can be calculated based on reference homozygous and heterozygous samples.

Alternatively, zygosity status of plants comprising EE-GH7 can also be determined based on copy number analysis, using the Taqman chemistry and principles of Real-Time PCR. The alternative method will typically include a EE-GH7 specific reaction to quantify the EE-GH7 copy number, and a endogenous gene-specific reaction for normalization of the EE-GH7 copy number. Samples containing the EE-GH7 event in a homozygous state will have a relative copy number that is two-fold higher than hemizygous samples. Azygous samples will not amplify the EE-GH7 sequence in such a method.

Furthermore, detection methods specific for elite event EE-GH7 which differ from PCR based amplification methods can also be developed using the elite event specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage", incorporated herein by reference). To this end, the target sequence is hybridized with a labeled first nucleic acid oligonucleotide comprising the nucleotide sequence of SEQ ID No 1 from nucleotide 1218 to nucleotide 1235 or its complement or said labeled nucleic acid probe comprising the nucleotide sequence of SEQ ID No 1 from nucleotide 8015 to 8032 or its complement and is further hybridized with a second nucleic acid oligonucleotide comprising the nucleotide sequence of SEQ ID No 1 from nucleotide 1200 to nucleotide 1217 or its complement or said labeled nucleic acid probe comprising the nucleotide sequence of SEQ ID No 1 from nucleotide 8033 to nucleotide 8050 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification.

A "kit" as used herein refers to a set of reagents for the purpose of performing the method of the invention, more particularly, the identification of the elite event EE-GH7 in biological samples or the determination of the zygosity status of EE-GH7 containing plant material. More particularly, a preferred embodiment of the kit of the invention comprises at least one or two specific primers, as described above for identification of the elite event, or three specific primers, or two specific primers and one specific probe, as described above for the determination of the zygosity status. Optionally, the kit can further comprise any other reagent described herein in the PCR Identification Protocol or any of the other protocols as described herein for EE-GH7 detection. Alternatively, according to another embodiment of this invention, the kit can comprise a specific probe, as described above, which specifically hybridizes with nucleic acid of biological samples to identify the presence of EE-GH7 therein. Optionally, the kit can further comprise any other reagent (such as but not limited to hybridizing buffer, label) for identification of EE-GH7 in biological samples, using the specific probe.

The kit of the invention can be used, and its components can be specifically adjusted, for purposes of quality control (e.g., purity of seed lots), detection of the presence or absence of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology Center). Sequences are indicated as "essentially similar" when such sequences have a sequence identity of at least about 75%, particularly at least about 80%, more particularly at least about 85%, quite particularly at least about 90%, especially at least about 95%, more especially at least about 98%, or at least about 99%. It is clear that when RNA sequences are said to be essentially similar or have a certain degree of sequence identity with DNA sequences, thymidine (T) in the DNA sequence is considered equal to uracil (U) in the RNA sequence. Also, it is clear that small differences or mutations may appear in DNA sequences over time and that some mismatches can be allowed for the event-specific primers or probes of the invention, so any DNA sequence indicated herein in any embodiment of this invention for any 3' or 5' flanking DNA or for any insert or foreign DNA or any primer or probe of this invention, also includes sequences essentially similar to the sequences provided herein, such as sequences hybridizing to or with at least 90%, 95%, 96%, 97%, 98%, or at least 99% sequence identity to the sequence given for any 3' or 5' flanking DNA, for any primer or probe or for any insert or foreign DNA of this invention.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR Identification Protocol), whereby the specificity is determined by the presence of positive and negative controls.

The term "hybridizing" as used herein when referring to specific probes, refers to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbor Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological sample is a sample of a plant, plant material or products comprising plant material. The term "plant" is intended to encompass cotton (*Gossypium hirsutum*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for EE-GH7, implying the presence of nucleic acids in the samples. Thus the methods referred to herein for identifying elite event EE-GH7 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, such as promoter and transcript termination sequences.

The present invention also relates to the development of an elite event EE-GH7 in cotton plants comprising this event, the progeny plants and seeds comprising elite event EE-GH7 obtained from these plants and to the plant cells, or plant material derived from plants comprising this event. Plants comprising elite event EE-GH7 can be obtained as described in Example 1. This invention also relates to seed comprising elite event EE-GH7 deposited at the ATCC under deposit number PTA-122856 or derivatives therefrom comprising elite event EE-GH7.

"Derivatives (of seed)" as used herein, refers to plants which can be grown from such seed, progeny resulting from crossing or backcrossing, as well as plant cells, organs, parts, tissue, cell cultures, protoplasts, and plant material of same.

Cotton plants or plant material comprising EE-GH7 can be identified according to any one of the identification protocols for EE-GH7 as described in the Examples, including the PCR Identification Protocol described for EE-GH7 in Example 2.1, the real-time PCR assays as described in Example 2.2, or the end-point TaqMan as described in Example 2.3. Briefly, cotton genomic DNA present in the biological sample is amplified by PCR using a primer which specifically recognizes a sequence within the 5' or 3' flanking sequence of EE-GH7 such as the primer with the sequence of SEQ ID NO: 3, SEQ ID No. 5 or SEQ ID No. 11, and a primer which recognizes a sequence in the foreign DNA, such as the primer with the sequence of SEQ ID No. 4 or SEQ ID No. 6, or with a primer which recognizes the 5' or 3' flanking sequence of EE-GH7 and the foreign DNA contiguous therewith, such as the primer with the sequence of SEQ ID No. 13. DNA primers which amplify part of an endogenous cotton sequence are used as positive control for the PCR amplification. If upon PCR amplification, the material yields a fragment of the expected size or gives rise to fluorescence of the expected fluorescent label, the material contains plant material from a cotton plant harboring elite event EE-GH7.

Plants harboring EE-GH7 are characterized by their glyphosate tolerance, as well as by their tolerance to HPPD inhibitors such as isoxaflutole. Cotton plants in different commercially available varieties harboring EE-GH7 are also characterized by having agronomical characteristics that are comparable to the corresponding non-transgenic isogenic commercially available varieties, in the absence of herbicide application. It has been observed that the presence of a foreign DNA in the insertion region of the cotton plant genome described herein, confers particularly interesting phenotypic and molecular characteristics to the plants comprising this event.

One embodiment of this invention provides an elite event in cotton plants, obtainable by insertion of 2 transgenes at a specific location in the cotton genome, which elite event confers tolerance to glyphosate and an HPPD inhibitor herbicide such as isoxaflutole on such cotton plants, and wherein such elite event has an agronomic performance essentially similar to isogenic lines (as used herein, "isogenic lines" or "near-isogenic lines" are cotton lines of the same genetic background but lacking the transgenes, such as plants of the same genetic background as the plant used for transformation, or segregating sister lines having lost the transgenes). Particularly, the current invention provides an elite event in cotton plants, wherein the insertion or presence of said elite event in the genome of such cotton plants does not appear to cause an increased susceptibility to disease, does not cause a yield penalty or reduced fiber quality, or does not cause increased lodging, as compared to isogenic lines. Hence, the current invention provides an elite event in cotton plants, designated as EE-GH7, which results in cotton plants that can tolerate the application of glyphosate and HPPD inhibitor herbicide without negatively affecting the yield or of fiber quality parameters of said cotton plants compared to isogenic lines, which cotton plants are not statistically significant different in their disease susceptibility, or lodging, from isogenic cotton plants. These characteristics make the current elite event a valuable tool in a weed resistance management program by providing tolerance to two distinct modes of action in cotton.

Provided herein is also a cotton plant or part thereof comprising event EE-GH7, wherein representative cotton seed comprising event EE-GH7 has been deposited under ATCC accession number PTA-122856. Further provided herein are seeds of such plants, comprising such event, as well as a cotton product produced from such seeds, wherein said cotton product comprises event EE-GH7. Such cotton product can be cotton fiber or a product comprising such cotton fiber. Particularly, such cotton product comprises a nucleic acid that produces an amplicon diagnostic or specific for event EE-GH7, such amplicon comprising SEQ ID No. 3 or 4. Also provided herein is a method for producing a cotton product, comprising obtaining a cotton plant or fiber comprising event EE-GH7, and producing such cotton product therefrom.

Also provided herein is a cotton plant, which is progeny of any of the above cotton plants, and which comprises event EE-GH7.

Further provided herein is a method for producing a cotton plant tolerant to glyphosate and/or isoxaflutole herbicides, comprising introducing into the genome of such plant event EE-GH7, particularly by crossing a first cotton plant lacking event EE-GH7 with a cotton plant comprising EE-GH7, and selecting a progeny plant tolerant to glyphosate and/or isoxaflutole.

Also provided herein is a glyphosate and/or isoxaflutole tolerant plant with acceptable agronomical characteristics and, particularly having acceptable fiber quality parameters, comprising a 2mEPSPS and HPPD protein, and capable of producing an amplicon diagnostic for event EE-GH7. Also provided herein are the specific isolated amplicons (DNA sequence fragments) as such, that can be obtained using the specific detection tools described herein, particularly amplicons including in their sequence a DNA fragment originating from plant DNA and a DNA fragment foreign or heterologous to such plant, such as the DNA inserted in the plant genome by transformation, as defined herein.

Further provided herein is a method for controlling weeds in a field of cotton plants comprising event EE-GH7, or a field to be planted with such cotton plants, comprising treating the field with an effective amount of an isoxaflutole-based herbicide, wherein such plants are tolerant to such herbicide.

Further provided herein is a DNA comprising the sequence of SEQ ID No 1 or a sequence essentially similar thereto, and any plant, cell, tissue or seed, particularly of cotton, comprising such DNA sequence, such as a plant, cell, tissue, or seed comprising EE-GH7. Also included herein is any cotton plant, cell, tissue or seed, comprising the DNA sequence (heterologous or foreign to a conventional cotton plant, seed, tissue or cell) of SEQ ID No. 1, or comprising a DNA sequence with at least 99% or 99.5% sequence identity to the sequence of SEQ ID No. 1.

Also described is a chimeric DNA comprising a foreign DNA, wherein the sequence of said foreign DNA consists of the sequence of SEQ ID No. 1 from nucleotide 1218 to nucleotide 8032, flanked by a 5' and a 3' flanking region, wherein the 5' flanking region immediately upstream of and contiguous with said foreign DNA is characterized by a sequence consisting of the sequence of SEQ ID No. 1 from nucleotide 1 to nucleotide 1217, and wherein the 3' flanking region immediately downstream of and contiguous with said foreign DNA is characterized by a sequence consisting of the sequence of SEQ ID No. 1 from nucleotide 8033 to 9328.

Chimeric DNA refers to DNA sequences, including regulatory and coding sequences that are not found together in nature. Accordingly, a chimeric DNA may comprise DNA regions adjacent to each other that are derived from different sources, or which are arranged in a manner different from that found in nature. A chimeric DNA can consist of the sequence of SEQ ID No. 1.

Also provided herein is a transgenic cotton plant, plant cell, tissue, or seed, comprising in their genome event EE-GH7 characterized by a nucleic acid molecule comprising a nucleotide sequence essentially similar to SEQ ID No. 1 from nucleotide 1207 to nucleotide 1228 and a nucleic acid molecule comprising a nucleotide sequence essentially similar to SEQ ID No. 1 from nucleotide 8022 to 8043, or the complement of said sequences, as well as a cotton plant, plant cell, tissue, or seed, comprising in their genome event EE-GH7 characterized by a nucleic acid molecule comprising a nucleotide sequence essentially similar to SEQ ID No. 1, or the complement of said sequences.

Even further provided herein is a cotton plant, cell, tissue or seed, comprising EE-GH7, characterized by comprising in the genome of its cells a nucleic acid sequence with at least 80%, 90%, 95% or 100% sequence identity to SEQ ID No. 1 from nucleotide 1207 to nucleotide 1228 and a nucleic acid sequence with at least 80%, 90%, 95% or 100% sequence identity to SEQ ID No. 1 from nucleotide 8022 to 8043, or the complement of said sequences.

The term "isoxaflutole", as used herein, refers to the herbicide isoxaflutole [i.e. (5-cyclopropyl-4-isoxazolyl)[2-(methylsulfonyl)-4-(trifluoromethyl)phenyl]methanone], the active metabolite thereof, diketonitrile, and any mixtures or solutions comprising said compounds. HPPD inhibiting herbicides useful for application on the event of this invention are the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-fione; other isoxazoles; and the pyrazolinates, e.g. topramezone [i.e. [3-(4,5-dihydro-3-isoxazolyl)-2-methyl-4-(methylsulfonyl) phenyl](5-hydroxy-1-methyl-1H-pyrazol-4-yl)methanone], and pyrasulfotole [(5-hydroxy-1,3-dimethylpyrazol-4-yl(2-mesyl-4-trifluaromethylphenyl) methanone]; or pyrazofen [2-[4-(2,4-dichlorobenzoyl)-1,3-dimethylpyrazol-5-yloxy]acetophenone].

In one embodiment of this invention, a field to be planted with cotton plants containing the EE-GH7 event, can be treated with an HPPD inhibitor herbicide, such as isoxaflutole ('IFT'), or with glyphosate, or with both an HPPD inhibitor herbicide and glyphosate, before the cotton is sown, which cleans the field of weeds that are killed by the HPPD inhibitor and/or glyphosate, allowing for no-till practices, followed by planting or sowing of the cottons in that same pre-treated field later on (burndown application using an HPPD inhibitor herbicide). The residual activity of IFT will also protect the emerging and growing cotton plants from competition by weeds in the early growth stages. Once the cotton plants have a certain size, and weeds tend to re-appear, glyphosate, or an HPPD inhibitor-glyphosate mixture, can be applied as post-emergent herbicide over the top of the plants.

In another embodiment of this invention, a field in which seeds containing the EE-GH7 event were sown, can be treated with an HPPD inhibitor herbicide, such as IFT, before the cotton plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing cotton plants have no competition by weeds (pre-emergence application of an HPPD inhibitor herbicide). Once the cotton plants have a certain size, and weeds tend to re-appear, glyphosate—or an HPPD inhibitor-glyphosate mixture—can be applied as post-emergent herbicide over the top of the plants.

In another embodiment of this invention, plants containing the EE-GH7 event, can be treated with an HPPD inhibitor herbicide, such as IFT, over the top of the cotton plants that have emerged from the seeds that were sown, which cleans the field of weeds killed by the HPPD inhibitor, which application can be together with (e.g., in a spray tank mix), followed by or preceded by a treatment with glyphosate as post-emergent herbicide over the top of the plants (post-emergence application of an HPPD inhibitor herbicide (with or without glyphosate)).

Also, in accordance with the current invention, cotton plants harboring EE-GH7 may be treated with the following insecticides, herbicides or fungicides or cotton seeds harboring EE-GH7 may be coated with a coat comprising the following insecticides, herbicides or fungicides:

Cotton Herbicides:
Carfentrazone, Clethodim, Diuron, Fluazifop-butyl, Flumioxazin, Fluometuron, Glufosinate, Glyphosate, Isoxaflutole, MSMA, Norflurazon, Oxyfluorfen, Pendimethalin, Prometryn, Pyrithiobac-sodium, Tepraloxydim, Thidiazuron, Trifloxysulfuron, Trifluralin.

Cotton Insecticides:
Abamectin, Acephate, Acetamiprid, Aldicarb, Azadirachtin, Bifenthrin, Chlorantraniliprole (Rynaxypyr), Chlorpyrifos, Clothianidin, Cyantraniliprole (Cyazypyr), (beta-)Cyfluthrin, gamma-Cyhalothrin, lambda-Cyhalothrin, Cypermethrin, Deltamethrin, Diafenthiuron, Dinotefuran, Emamectin-benzoate, Flonicamid, Flubendiamide, Fluensulfone, Fluopyram, Flupyradifurone, Imicyafos, Imidacloprid, Indoxacarb, Metaflumizone, Pymetrozine, Pyridalyl, Pyrifluquinazon, Spinetoram, Spinosad, Spiromesifen, Spirotetramat, Sulfoxaflor, Thiacloprid, Thiamethoxam, Thiodicarb, Triflumuron, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{([5-(trifluoromethyl)-1H-tetrazol-1-yl]methyl}-1H-pyrazole-5-carboxamide, 1-{2-fluoro-4-methyl-5-[(2,2,2-trifluorethyl) sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus*,

*Bacillus firmus* strain 1-1582, *Bacillus subtilis*, *Bacillus subtilis* strain GB03, *Bacillus subtilis* strain QST 713, Metarhizium anisopliae F52.

Cotton Fungicides:
Azoxystrobin, N-[9-(dichloromethylene)-1,2,3,4-tetra-hydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Ipconazole, Iprodione, Isopyrazam, Isotianil, Mancozeb, Maneb, Mefenoxam, Metalaxyl, Metominostrobin, Pencycuron, Penflufen, Penthiopyrad, Picoxystrobin, Propineb, Prothioconazole, Pyraclostrobin, Quintozene, Sedaxane, Tebuconazole, Tetraconazole, Thiophanate-methyl, Triadimenol, Trifloxystrobin, *Bacillus firmus*, *Bacillus firmus* strain I-1582, *Bacillus subtilis*, *Bacillus subtilis* strain GB03, *Bacillus subtilis* strain QST 713.

The following examples describe the development and identification of elite event EE-GH7, the development of different cotton lines comprising this event, and the development of tools for the specific identification of elite event EE-GH7 in biological samples.

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy R D D (ed.) (1993) Plant Molecular Biology LabFax, BIOS Scientific Publishers Ltd., Oxford and Blackwell Scientific Publications, Oxford" and in "Brown TA, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com".

It should be understood that a number of parameters in any lab protocol such as the PCR protocols in the below Examples may need to be adjusted to specific laboratory conditions, and may be modified slightly to obtain similar results. For instance, use of a different method for preparation of DNA or the selection of other primers in a PCR method may dictate other optimal conditions for the PCR protocol. These adjustments will however be apparent to a person skilled in the art, and are furthermore detailed in current PCR application manuals.

The sequence listing contained in the file named "BCS16-2014_ST25.txt", which is 20 kilobytes (size as measured in Microsoft Windows®), contains 13 sequences SEQ ID NO: 1 through SEQ ID NO: 13 is filed herewith by electronic submission and is incorporated by reference herein.

In the description and examples, reference is made to the following sequences:
SEQ ID No. 1: nucleotide sequence of foreign DNA and plant flanking sequences in EE-GH7
SEQ ID No. 2: pre-insertion plant DNA sequence
SEQ ID No. 3: primer PRIM0728
SEQ ID No. 4: primer PRIM0643
SEQ ID No. 5: primer PRIM0638
SEQ ID No. 6: primer PRIM0639
SEQ ID No. 7: probe TM1576
SEQ ID No. 8: primer KVM157
SEQ ID No. 9: primer KVM158
SEQ ID No. 10: probe TM1304
SEQ ID No. 11: primer PRIM0726
SEQ ID No. 12: primer PRIM0733
SEQ ID No. 13: primer PRIM0731

EXAMPLES

1. Transformation of *Gossypium hirsutum* with Herbicide Tolerance Genes 1.1. Description of the Foreign DNA Comprising the 2mepeps and hppdPf-W336-1 Pa Chimeric Genes EE-GH7 cotton was developed through *Agrobacterium*-mediated transformation using the vector pTSIH09 containing hppdPf-W336-1 Pa and 2mepsps expression cassettes.
(i) The double mutant 5-enol pyruvylshikimate-3-phosphate synthase (2mepsps) gene that encodes for the 2mEPSPS protein. The 2mepsps coding sequence was developed by introducing a point mutation at positions 102 (substitution of threonine by isoleucine) and at position 106 (substitution of proline by serine) of the wild-type epsps gene cloned from maize (*Zea mays*) (Lebrun et al, 1997 (WO9704103)). Expression of the 2mEPSPS protein confers tolerance to glyphosate herbicides.
(ii) The hppdPf-W336-1 Pa gene encodes for the HPPD W336 protein. The hppdPf-W336-1Pa coding sequence was developed by introducing a single point mutation resulting in the replacement of the amino acid glycine 336 with a tryptophan of the wild type hppd gene derived from Pseudomonasfluorescens (Boudec et al., 2001, (U.S. Pat. No. 6,245,968B1)). Expression of the HPPD W336 protein confers tolerance to HPPD inhibitor herbicides, such as isoxaflutole.

Plasmid pTSIH09 is a plant transformation vector which contains a chimeric 2mepsps gene and a chimeric hppdPf-W336-1 Pa gene located between the right T-DNA border (RB) and the left T-DNA border (LB). A description of the genetic elements comprised between the right and left T-DNA border is given in Table 1 below. The nucleotide sequence is represented in SEQ ID No. 1.

TABLE 1

Nucleotide positions of the DNA of pTSIH09 inserted in the plant genome (nt 1218-8032 of SEQ ID No. 1)

| Nucleotide positions | Orientation | Description and references |
|---|---|---|
| 1277-1943 | complement | 3'histonAt: sequence including the 3' untranslated region of the histone H4 gene of *Arabidopsis thaliana* (Chabouté et al., 1987, Plant Molecular Biology, 8, 179-191) |
| 1960-3036 | complement | hppdPf W336-1Pa: sequence encoding the 4-hydroxyphenylpyruvate dioxygenase of *Pseudomonas fluorescens* strain A32 modified by the replacement of the amino acid Glycine 336 with a Tryptophane, as described by Boudec et al. (2001) U.S. Pat. No. 6,245,968 B1 |
| 3037-3408 | complement | TPotp Y-1Pa: sequence encoding an optimized transit peptide derivative (position 55 changed into Tyrosine), containing sequence of the RuBisCO small subunit genes of *Zea mays* (corn) and *Helianthus annuus* (sunflower), as described by Lebrun et al. (1996) U.S. Pat. No. 5,510,471 |
| 3417-3929 | complement | Pcsvmv XYZ: sequence including the promoter region of the Cassava Vein Mosaic Virus |

TABLE 1-continued

Nucleotide positions of the DNA of pTSIH09 inserted in the plant genome (nt 1218-8032 of SEQ ID No. 1)

| Nucleotide positions | Orientation | Description and references |
|---|---|---|
| | | (Verdaguer et al., (1996) Plant Mol Biol, 31, 1129). |
| 4028-4944 | | Ph4a748 ABC: sequence including the promoter region of the histone H4 gene of *Arabidopsis thaliana* (Chabouté et al., 1987, Plant Molecular Biology, 8, 179-191). |
| 4984-5449 | | intron1 h3At: first intron of gene II of the histone H3.III variant of *Arabidopsis thaliana* (Chaubet et al., 1992) Journal of Molecular Biology, 225, 569-574. |
| 5463-5834 | | TPotp C: sequence encoding the optimized transit peptide, containing sequence of the RuBisCO small subunit genes of *Zea mays* (corn) and *Helianthus annuus* (sunflower), as described by Lebrun et al. (1996) U.S. Pat. No. 5,510,471 |
| 5835-7172 | | 2mepsps: sequence encoding the double-mutant 5-enol-pyruvylshikimate-3-phosphate synthase gene of *Zea mays* (corn) (Lebrun et al., 1997) WO9704103-A 1 |
| 7193-7859 | | 3'histonAt: sequence including the 3' untranslated region of the histone H4 gene of *Arabidopsis thaliana* (Chabouté et al., 1987) Plant Molecular Biology, 8, 179-191. |

1.2. Event EE-GH7

The T-DNA vector pTSIHO9 was introduced into *Agrobacterium tumefaciens* C58C1Rif (pEHA101) and cotton were selected using spectinomycin and streptomycin according to methods known in the art.

The *Agrobacterium* strains were used to transform the cotton var. "Coker 312" according to methods known in the art and transgenic plants were selected in vitro for tolerance to glyphosate (1.0-1.5 mM), followed by regeneration of transformed plant cells into transgenic fertile cotton plants. T0 plants were treated with tembotrione (HPPD-inhibitor herbicides) to select for the expression of the hppdPfw336-1 Pa genes. The surviving plants were then self-pollinated to generate T1 seed. Subsequent T2 to T7 generations were produced through self-pollination. Subsamples of the T1 and T2 plants were sprayed with glyphosate to ensure expression of the 2mepsps gene at those generations. In the T3 through T7 generations which were grown in the field, each selfed generation was sprayed with glyphosate to ensure the expression of the 2mepsps gene.

1.2.1 Identification of Elite Event EE-GH7

Elite event EE-GH7 was selected based on an extensive selection procedure based on trait efficacy, good expression and stability of the herbicide tolerance genes, and its compatibility with optimal agronomic characteristics such as plant height, height to node, boll retention, stand, vigor, fiber length, fiber strength and lint yield were evaluated. Cotton plants containing this event were selected from a wide range of different transformation events obtained using the same chimeric genes. Parameters used in the selection of this event were: a) acceptable tolerance to isoxaflutole herbicide application in field trials, b) acceptable tolerance to glyphosate herbicide application in field trials, c) an insertion of the herbicide tolerance transgenes at a single locus in the cotton plant genome, with absence of vector backbone, c) overall agronomy similar to the parent plants used for transformation (maturity, lodging, disease susceptibility, etc.), e) no yield penalty or no change in fiber quality characteristics caused by the insertion of the transforming DNA (as compared to a corresponding isogenic line without the event, such as the plant line used for transformation or commercial varieties, grown under the same conditions), f) stable inheritance of the insert, and g) phenotypic stability.

1.2.1.1 Structural Stability of the Event

Structural stability of EE-GH7 was determined using Southern Blot analysis in T1, T3, T4, BC1F2 and BC2F3 generations. The results of these southern blot analyses demonstrate structural stability of the event in all tested generations.

1.2.1.2 Inheritance of the Event

Inheritance of the foreign DNA insert was tested in F2, BC1F2 and BC2F2 generations by testing the genotype of hppdPfW336-1 Pa and 2mepsps genes by PCR analysis. Segregation ratios determined for three generations of EE-GH7 cotton confirmed that the hppdPfW336-1 Pa and 2mepsps genes contained within the EE-GH7 insert are inherited in a predictable manner and as expected for a single insertion. These data are consistent with Mendelian principles and support the conclusion that the EE-GH7 event consists of a single insert integrated into a single chromosomal locus within the cotton nuclear genome.

1.2.1.3 Stability of Protein Expression

Protein expression levels of HPPD W336 and 2mEPSPS proteins were determined by sandwich enzyme-linked immunosorbent assay (ELISA) in leaf and fuzzy seed samples collected from three generations (T4, T5, and BC2F4) of EE-GH7 cotton.

Mean expression levels of HPPD W336 in leaf at 4-6 Leaf growth stage (BBCH 14-16) across T4, T5, and BC2F4 generation were 442.73, 421.06 and 410.89 µg/g DW, respectively. Mean expression levels of HPPD W336 in fuzzy seed at maturity growth stage (BBCH 83-97) across the three generations were 42.83, 42.45, and 34.97 µg/g DW, respectively.

Mean expression levels of 2mEPSPS in leaf at 4-6 Leaf growth stage (BBCH 14-16) across T4, T5, and BC2F4 generations were 1078.03, 1115.46 and 1498.30 µg/g DW, respectively. Mean expression levels of 2mEPSPS in fuzzy seed at maturity growth stage (BBCH 83-97) across the three generations (T4, T5, and BC2F4) were 163.07, 160.49, and 147.80 µg/g DW, respectively. HPPD W336 and 2mEPSPS, respectively, exhibited similar mean expression levels in leaf and fuzzy seed across the three generations. Therefore, the protein expression of HPPD W336 and 2mEPSPS was demonstrated to be stable over three generations.

1.2.1.4 Agronomic Performance and Tolerance to Isoxaflutole (IFT) and Glyphosate (GLY)

In agronomic equivalency trials, plants comprising EE-GH7 perform similarly to null segregants and wild-type counterparts. Plants comprising EE-GH7 had normal agronomic characteristics as compared to the corresponding non-transgenic plants.

Tolerance of plants comprising EE-GH7 to IFT, to glyphosate and to combinations thereof, was tested at different locations in the field. The plants comprising EE-GH7 showed good tolerance to IFT alone, in particular when IFT was applied before emergence. Plants comprising EE-GH7 also show good tolerance to glyphosate applied post emergence, and to a combination of IFT and glyphosate, especially when IFT was applied pre emergence and glyphosate was applied post emergence. Importantly, the glyphosate tolerance of plants comprising EE-GH7 is equal to or better than glyphosate tolerance of the elite glyphosate tolerant event EE-GH3 of WO2007/017186. Currently available data appear to indicate a performance which is at least equal to, or better than the performance of plants comprising EE-GH7 over plants comprising the hppd and epsps chimeric genes as described in WO2013/026740.

To evaluate the agronomic performance of GHB811 cotton under field conditions representative of commercial cultivation, a multi-site field evaluation was undertaken. The agronomic assessment included 15 locations (seven sites conducted in one year and eight sites conducted in another year) representative of diverse cotton growing regions.

All plots within a field site were subjected to the same growing conditions and management (i.e. cultivation, irrigation, fertilizer, maintenance pesticide treatments). Each plot within each field trial was identically sized.

The EE-GH7 cotton plots treated with the trait specific herbicide received one spray application of each trait-specific herbicide. One application of IFT was made at a rate of 100.3 to 115.2 grams active ingredient per hectare (g ai/ha) before or shortly after emergence (BBCH 00 to 13). One application of GLY was made at a rate of 1067 to 1222 g ai/ha at the six to nine leaf growth stage (BBCH 16 to 19).

The following agronomic parameters were measured throughout the growing season at each field trial site. Data are reported for each individual plot in each field trial.

Continuous Parameters:
Early Stand Counts
Percent Ground Cover
Days and Heat Units to First Flower
Days and Heat Units to First Open Bolls
Percent Open Bolls
Final Stand Count
Boll Properties
Seed Cotton Yield
Lint Yield
Link (Fiber) Properties
Categorical Parameters:
Abiotic Stressor Rating
Disease Stressor Rating
Insect Stressor Rating
Boll Type
Plant Lodging Agronomic observations for the non-GM counterpart (Coker 312) were compared to EE-GH7 cotton not treated with IFT and GLY, and also compared to EE-GH7 cotton treated with IFT and GLY.

Statistically significant differences were detected for the continuous parameters Final Stand Count, Seed Cotton Yield, Lint Yield, and Height to Node Ratio between the non-GM counterpart (Coker 312) and EE-GH7 cotton not treated with trait-specific herbicides. Statistically significant differences were also detected for Boll Weight between the non-GM counterpart and both EE-GH7 cotton entries (treated and not treated). All mean values of the continuous agronomic parameters of EE-GH7 cotton (treated or not treated) were within the range of the reference varieties. Thus, statistically significant differences were considered not biologically relevant.

The combined site summary of statistical results for the categorical parameters of Boll Type, Plant Lodging, four insect stressor ratings, four disease stressor ratings, and four abiotic stressor ratings were determined. No statistically significant differences, as defined by CMH test p-values <0.05, were detected for thirteen of the fourteen categorical parameters. Statistically significant differences were observed for the third disease stressor rating between the non-GM counterpart and both EE-GH7 cotton entries (treated and not treated). All mean values for EE-GH7 cotton (treated or not treated) in the third disease stressor rating fell within the range of the reference varieties and thus statistically significant differences were considered not biologically relevant.

Based on the agronomic assessment, EE-GH7 cotton demonstrated no biologically relevant differences from the non-GM counterpart and showed equivalent agronomic performance to non-GM reference varieties.

1.2.2 Identification of the Flanking Regions and Foreign DNA of Elite Event EE-GH7

The sequence of the regions flanking the foreign DNA comprising the herbicide tolerance genes in the EE-GH7 elite event was determined to be as follows:

1.2.2.1 Right (5') Flanking Region

The fragment identified as comprising the 5' flanking region was sequenced and its nucleotide sequence is represented in SEQ ID No. 1, nucleotides 1-1217.

1.2.2.2 Left (3') Flanking Region

The fragment identified as comprising the 3' flanking region was sequenced and its nucleotide sequence is represented in SEQ ID No. 1, nucleotides 8033-9328.

1.2.2.3 Foreign DNA Comprising the Herbicide Tolerance Genes of EE-GH7

Confirmed full DNA sequencing of the foreign DNA and flanking DNA sequences in EE-GH7 resulted in the sequence reported in SEQ ID No. 1. The sequence of the foreign DNA of elite event EE-GH7 comprising the herbicide tolerance genes is represented in SEQ ID No. 1, nucleotides 1218-8032. This foreign DNA is preceded immediately upstream and contiguous with the foreign DNA by the 5' flanking sequence of SEQ ID No 1 from nucleotide 1 to 1217 and is followed immediately downstream and contiguous with the foreign DNA by the 3' flanking sequence of SEQ ID No 1 from nucleotide 8033 to nucleotide 9328.

1.2.2.4 Identification of the Pre-Insertion Plant DNA

Pre-insertion plant DNA was amplified by PCR. The nucleotide sequence of the amplified fragment was identified (SEQ ID No. 2). Nucleotides 1218-1230 of SEQ ID No. 2 were deleted the EE-GH7 transgenic locus (target site deletion). Nucleotides 1-1217 of SEQ ID No. 2 correspond to the 5' flanking sequence of EE-GH7, and nucleotides 1231-2526 of SEQ ID No. 2 correspond to the 3' flanking sequence of EE-GH7.

2. Development of Identification Protocols for EE-GH7

2.1. Polymerase Chain Reaction for Detection of the EE-GH7 Event Specific Sequence 2.1.1 Primers Specific primers were developed which recognize sequences within the elite event.

A primer was developed which recognizes a sequence within the 5' flanking region of EE-GH7. A second primer was then selected within the sequence of the foreign DNA so that the primers span a sequence of about 126 nucleotides. The following primers were found to give clear and reproducible results in a PCR reaction on EE-GH7 DNA:

```
Forward primer targeted to the 5' flanking
sequence:
PRIM0728:
                                     (SEQ ID No.: 3)
5'-CTCCgAATAgTTCCATCAATTTTATCA-3'

Reverse primer targeted to the foreign DNA:
PRIM0643:
                                     (SEQ ID No.: 4)
5'-TgATCgggCCTTAATTAACCC-3'
```

Preferably, an appropriate taxon-specific reference system reaction must be performed on identical amounts of DNA of all samples analysed to demonstrate that the samples are in principle functional for PCR analysis. Such taxon-specific reference system may consist of primers targeting an endogenous sequence which are included in the PCR cocktail. These primers serve as an internal control in unknown samples and in the DNA positive control. A positive result with the endogenous primer-pair demonstrates that the samples are in principle functional for PCR analysis and there is ample DNA of adequate quality in the genomic DNA preparation for a PCR product to be generated.

2.1.2 Amplified Fragments

The expected amplified fragments in the PCR reaction are:

For primer pair PRIM0728-PRIM0643: 126 bp (EE-GH7 elite event)

2.1.3 Template DNA

Template DNA was be prepared using the AGOWA sbeadex Maxi Plant Kit. When using DNA prepared with other methods, a test run utilizing different amounts of template should be done. Usually 50 ng of genomic template DNA yields the best results.

2.1.4 Assigned Positive and Negative Controls

To avoid false positives or negatives, it was determined that the following positive and negative controls should be included in a PCR run:

No template control (DNA negative control). This is a PCR in which no DNA is added to the reaction. When the expected result, no PCR products, is observed this indicates that the PCR cocktail was not contaminated with target DNA.

A positive DNA control (genomic DNA sample known to contain the transgenic sequences). Successful amplification of this positive control demonstrates that the PCR was run under conditions which allow for the amplification of target sequences.

A negative DNA control (wild-type DNA control). This is a PCR in which the template DNA provided is genomic DNA prepared from a non-transgenic plant. When the expected result, no amplification of the event specific PCR product but amplification of the endogenous PCR product, is observed this indicates that there is no detectable transgene background amplification in a genomic DNA sample.

2.1.5 PCR Conditions

Optimal results were obtained under the following conditions (In describing the various conditions for optimal results is meant to provide examples of such conditions. Clearly one skilled in the art could vary conditions, reagents and parameters such as using other Taq polymerases, and achieve desirable results):

the PCR mix for 25 µl reactions contains:
50 ng template DNA
5.0 µl 5× Amplification Buffer (supplied by the manufacturer with the Taq polymerase)
0.25 µl 20 mM dNTP's
0.7 µl PRIM0728 (10 pmoles/µl)
0.7 µl PRIM0643 (10 pmoles/µl)
0.1 µl Taq DNA polymerase (5 units/µl)
water up to 25 µl the thermocycling profile to be followed for optimal results is the following:

|  |  |
|---|---|
|  | 4 min. at 95° C. |
| Followed by: | 1 min. at 95° C. |
|  | 1 min. at 60° C. |
|  | 2 min. at 72° C. |
|  | For 5 cycles |
| Followed by: | 30 sec. at 92° C. |
|  | 30 sec. at 60° C. |
|  | 1 min. at 72° C. |
|  | For 30 cycles |
| Followed by: | 10 minutes at 72° C. |

2.1.6 Agarose Gel Analysis

To optimally visualize the results of the PCR it was determined that about 25 µl of the PCR samples should be applied on a 3% agarose gel (Tris-borate buffer, ethidium-bromide stained) with an appropriate molecular weight marker (e.g. 50 bp ladder).

2.1.7 Validation of the Results

It was determined that data from transgenic plant DNA samples within a single PCR run and a single PCR cocktail should not be acceptable unless 1) the DNA positive control shows the expected PCR product (transgenic fragment and, if included, endogenous fragment), 2) the DNA negative control is negative for PCR amplification (no fragment), and 3) the wild-type DNA control is negative for PCR amplification for the transgenic fragment and, if included, positive for the endogenous fragment.

When following the PCR Identification Protocol for EE-GH7 as described above, lanes showing visible amounts of the transgenic PCR products of the expected sizes, indicate that the corresponding plant from which the genomic template DNA was prepared, has inherited the EE-GH7 elite event. Lanes not showing visible amounts of the transgenic PCR product indicate that the corresponding plant from which the genomic template DNA was prepared, does not comprise the elite event.

2.1.8 Use of Discriminating PCR Protocol to Identify EE-GH7

Before attempting to screen unknowns, a test run, with all appropriate controls, is performed. The developed protocol might require optimization for components that may differ between labs (template DNA preparation, Taq DNA polymerase, quality of the primers, dNTP's, thermocyler, etc.).

Leaf material from a number of cotton plants, some of which comprising EE-GH7 were tested according to the above-described protocol. Samples from elite event EE-GH7 and from cotton wild-type were taken as positive and negative controls, respectively.

Figure 2:
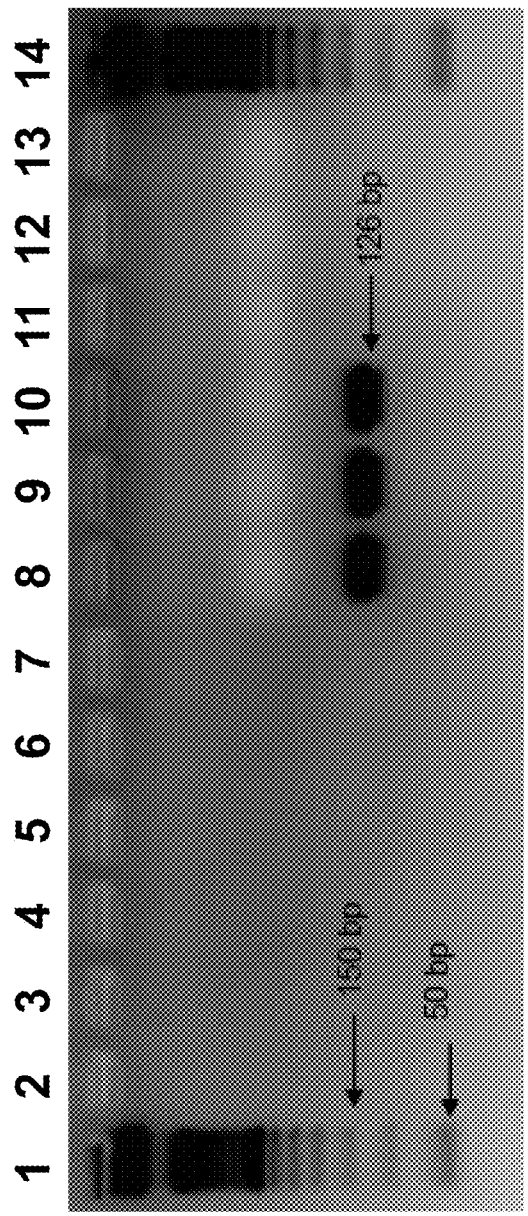
FIG. 2: Results obtained by the PCR Identification Protocol developed for EE-GH7. Loading sequence of the gel: Lane 1: Molecular weight marker (50 bp ladder); lanes 2, 3 and 4: negative control (no template); lanes 5, 6 and 7: DNA from wild type cotton plants; lanes 8, 9 and 10: DNA samples from cotton plants comprising the transgenic event EE-GH7; lanes 11, 12 and 13: negative control (no template); lane 14: Molecular Weight Marker (50 bp ladder). Numbers indicate the size of the marker fragments and the EE-GH7 specific fragment.

FIG. 2 illustrates the result obtained with the elite event PCR Identification Protocol for EE-GH7 on a number of cotton plant samples. The samples in lanes 2, 3, 4, 11, 12 and 13 represent the negative control (no template); lanes 5, 6 and 7 contain DNA from wild type cotton plants. Lanes 8, 9 and 10 comprise samples from cotton transformation event EE-GH7, lanes 1 and 14 represent the Molecular Weight Marker (50 bp ladder). It can be seen that, specifically for cotton transformation event EE-GH7, a 126 bp PCR fragment is produced.

2.2. Real-Time PCR Assay for Detection of the EE-GH7 Event Specific Sequence 2.2.1 Real-Time PCR Assay for EE-GH7 Detection in Bulked Seeds A Real-Time PCR assay is set up to detect low level presence of EE-GH7 in bulked seeds.

The following primers were applied in this target PCR reaction:

```
Forward primer targeted to the 5' flanking
sequence:
PRIM0638
                                     (SEQ ID No. 5)
5'-CgAATAgTTCCATCAATTTTATCATTTATg-3'

Reverse primer targeted to the foreign DNA
sequence:
PRIM0639
                                     (SEQ ID No. 6)
5'-TCgggCCTTAATTAACCCg-3'
```

The expected amplified fragment in the PCR reaction from these primers is 120 bp.

```
Probe targeted to the junction 5' flanking—
foreign DNA sequence:
TM1576
                                     (SEQ ID No. 7)
5'-AgAACAACAgTACTgggC-3'
```

The TM1576 probe is labelled with FAM at the 5' end and with the non-fluorescent quencher MGBNFQ at the 3' end.

The target PCR reaction is performed on approximately 200 ng of template DNA prepared using the AGOWA sbeadex Maxi Plant Kit. When using DNA prepared with other methods, a test run using samples with known relative levels of EE-GH7 should be performed.

An appropriate taxon-specific reference system reaction must be performed on identical amounts of DNA of all samples analysed to demonstrate that the samples are in principle functional for PCR analysis.

For unknown test samples the PCR experiment should ideally include the appropriate positive and negative control samples, i.e.:

- No template control (DNA negative control). This is a PCR in which no DNA is added to the reaction. When the expected result (no PCR product) is observed for both the target and the reference system reaction this indicates that the PCR cocktail was not contaminated with target DNA.
- A positive DNA control (genomic DNA sample known to contain the transgenic sequences). Successful amplification of this positive control demonstrates that the PCR was run under conditions which allow for the amplification of target sequences.
- Also a negative DNA control (wild-type DNA control) can be added in this PCR. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

This protocol was validated using 2× PerfeCta qPCR Fastmix II, Low ROX supplied by Quanta Bioscience (catalog nr. 95120). Any other reaction buffer may be applied but the procedures need to be validated successfully with the appropriate set of positive and negative controls prior to analyzing samples of unknown content. Optimal results are obtained under the following conditions:

the PCR mix for 20 µl reactions contains:
  200 ng template DNA
  10 µl 2× PerfeCta qPCR Fastmix II, low ROX (Quanta Biosciences)
  0.5 µl PRIM0638 (10 pmoles/µl)
  0.5 µl PRIM0639 (10 pmoles/µl)
  0.5 µl TM1576 (10 pmoles/µl)
  Add water up to 20 µl the thermo-cycling profile to be followed for optimal results is the following:

| | |
|---|---|
| | 5 min. at 95° C. |
| Followed by: | 15 sec. at 95° C. |
| | 1 min. at 60° C. |
| | For 40 cycles |

Amplification of the target is measured real-time by measuring the FAM reporter dye during the step of 1 min. at 60° C.

Figure 3:
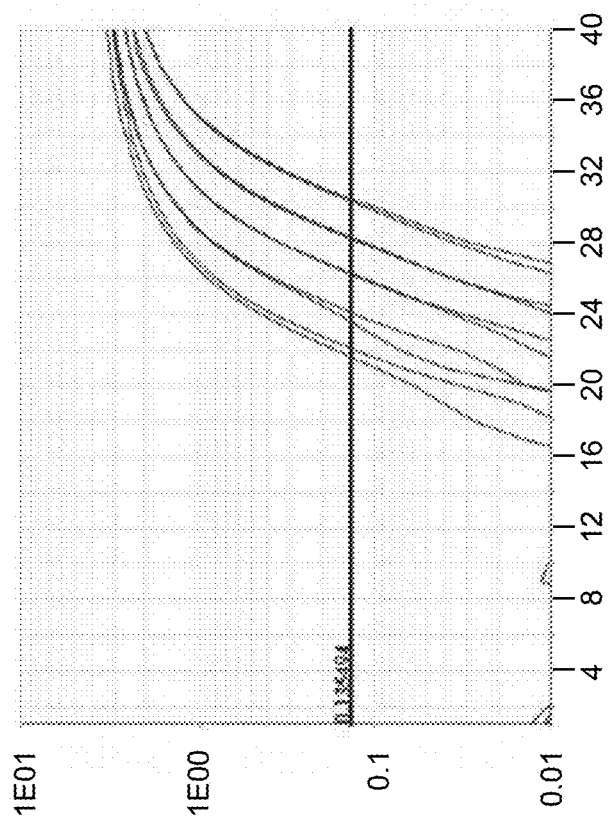
FIG. 3: Results of real-time PCR assay for detection of EE-GH7 in bulked seeds. The graph shows relative fluorescence in logarithmic scale for 5-fold dilutions of DNA comprising EE-GH7. The X-axis represents the PCR cycle. Horizontal bar: threshold level which is, for this experiment, at 0.135494.

Results of the Real-Time PCR Identification Protocol for EE-GH7 for 5-fold dilutions of genomic DNA comprising EE-GH7 are shown in FIG. 3. FIG. 3 shows that there is a clear correlation between the PCR cycle at which the threshold level is reached and the dilution of the DNA comprising EE-GH7.

2.2.2 Copy Real-Time PCR Assay for EE-GH7 for Determination of the Presence and the Zygosity on Individual Plants/Single Seeds A copy Real-Time PCR assay is set up to quantify the presence of EE-GH7 and to determine the zygosity of EE-GH7 in individual plants/single seeds.

The primers and probe applied in this target PCR reaction directed to the transgene DNA sequence are the same as described for the Real-Time PCR assay for EE-GH7 detection in bulked seeds as described in Example 2.2.1.:

```
Forward primer targeted to the 5' flanking
sequence:
PRIM0638
                                     (SEQ ID No. 5)
5'-CgAATAgTTCCATCAATTTTATCATTTATg-3'

Reverse primer targeted to the foreign DNA
sequence:
PRIM0639
                                     (SEQ ID No. 6)
5'-TCgggCCTTAATTAACCCg-3'
```

The expected amplified fragment in the PCR reaction from these primers is 120 bp.

Probe targeted to the junction 5' flanking—foreign DNA sequence:

```
TM1576
                                     (SEQ ID No. 7)
5'-AgAACAACAgTACTgggC-3'
```

The TM1576 probe is labelled with FAM at the 5' end and with the non-fluorescent quencher MGBNFQ at the 3' end.

The following primers targeting an endogenous sequence are also included in the PCR cocktail. These primers serve as an internal control in unknown samples and in the DNA positive control. A positive result with the endogenous primer-pair (presence of an PCR amplified fragment of 74 bp) demonstrates that there is ample DNA of adequate quality in the genomic DNA preparation for a PCR product to be generated. Suitable endogenous primers can be primers selected to recognize a housekeeping gene in cotton, such as:

Forward primer targeted to an endogenous target gene sequence:
KVM157:

(SEQ ID No.: 8)
5'-CACATgACTTAgCCCATCTTTgC-3'

Reverse primer targeted to an endogenous target gene sequence:
KVM158:

(SEQ ID No.: 9)
5'-CCCACCCTTTTTTggTTTAgC-3'

The expected amplified fragment in the PCR reaction from these primers is 74 bp.

Probe targeted to endogenous target gene sequence:

TM1304:
(SEQ ID No.: 10)
5'-TgCAggTTTTggTgCCACTgTgAATg-3'

The TM1304 probe is labelled with JOE at the 5' end and with the non-fluorescent quencher BHQ1 at the 3' end.

This protocol was validated using 2× PerfeCta qPCR Fastmix II, Low ROX supplied by Quanta Bioscience (catalog nr. 95120). Any other reaction buffer may be applied but the procedures need to be validated successfully with the appropriate set of positive and negative controls prior to analysing samples of unknown content. Optimal results are obtained under the following conditions:
    the PCR mix for 10 µl reactions contains:
        10 ng template DNA
        5 µl 2× PerfeCta qPCR Fastmix II, low ROX (Quanta Biosciences)
        0.5 µl PRIM0638 (10 pmoles/µl)
        0.5 µl PRIM0639 (10 pmoles/µl)
        0.5 µl KVM157 (10 pmoles/µl)
        0.5 µl KVM158 (10 pmoles/µl)
        0.1 µl TM1576 (10 pmoles/µl)
        0.1 µl TM1304 (10 pmoles/µl)
    Add water up to 10 µl
    the thermocycling profile to be followed for optimal results is the following:

| | |
|---|---|
| Followed by: | 5 min. at 95° C.<br>3 sec. at 95° C.<br>30 sec. at 60° C.<br>For 35 cycles |

Amplification of the target is measured real-time by measuring the FAM reporter dye during the step of 30 sec. at 60° C. and amplification of the endogenous control is measured real-time by measuring the JOE reporter dye during the step of 30 sec. at 60° C.

To avoid false positives or negatives, it was determined that the following positive and negative controls should be included in a PCR run:
    Homozygous control: a genomic DNA sample containing the target sequence described homozygously
    Hemizygous control: a genomic DNA sample containing the target sequence described hemizygously
    Wild type control (DNA negative control): a genomic DNA sample not containing the target sequence described
    No Template Control (NTC): a water sample Data analysis was performed using the ddCt method. In this method the zygosity for each test sample is calculated relative to a reference sample. For DNA samples hemizygous for EE-GH7, a copy number of 1 was calculated, whereas for DNA samples homozygous for EE-GH7 a copy number of 2 was calculated using this method, showing that it can be used to determine the zygosity status of EE-GH7.

2.3. End-Point TaqMan for Detection of the EE-GH7 Event Specific Sequence

The End-point TaqMan for EE-GH7 detection uses the same primers and probes as the copy Real-Time PCR assay for EE-GH7 detection on individual plants/single seeds as described under 2.2.2.
    the PCR mix for 10 µl reactions contains:
        10 ng template DNA
        5 µl 2× PerfeCta qPCR Fastmix II, low (Quanta Biosciences, cat no 95119)
        0.5 µl PRIM0638 (10 pmoles/µl)
        0.5 µl PRIM0639 (10 pmoles/µl)
        0.04 µl KVM157 (10 pmoles/µl)
        0.04 µl KVM158 (10 pmoles/µl)
        0.1 µl TM1576 (10 pmoles/µl)
        0.05 µl TM1304 (10 pmoles/µl)
    Add water up to 10 µl
    the thermocycling was the following:

| | |
|---|---|
| Followed by: | 5 min. at 95° C.<br>3 sec. at 95° C.<br>30 sec. at 60° C.<br>For 35 cycles |

Figure 4:
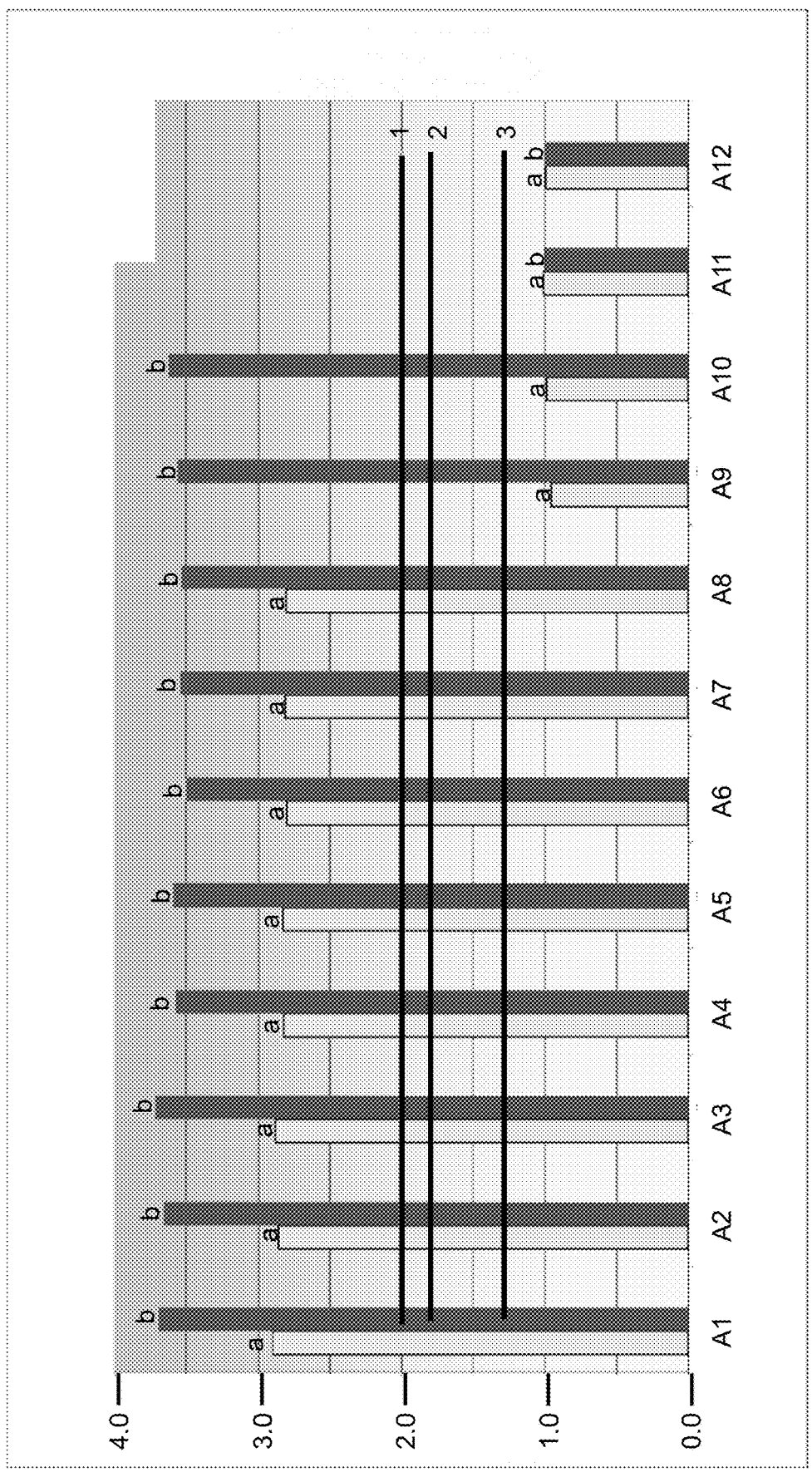
FIG. 4: Results of End-point TaqMan for EE-GH7 detection. Y-axis: Signal to background (S/B) ratio; X-axis: Sample number. White bars marked with "a": Target (EE-GH7); gray bars marked with "b": endogenous control; horizontal line marked with "1": lower level threshold for target (EE-GH7); horizontal line marked with "2": threshold for endogenous control; horizontal line marked with "3": Upper level negative control. Samples: A1-A8: samples comprising EE-GH7; A9 and A10: samples from wild type cotton plants not comprising EE-GH7; A11 and A12: negative control (no template).

Results for an end-point TaqMan PCR Identification Protocol for EE-GH7 detection are shown in FIG. 4. It is shown that samples comprising EE-GH7 (samples A1-A8) contain the EE-GH7 signal as well as the endogenous control signal above the threshold; the samples containing non-transformed cotton (samples A9 and A10) contain only endogenous control, but not EE-GH7 signal above the threshold, and the no template control (samples A11-A12) contain no signal above the threshold.

3. Protocol for the PCR-Based Determination of the Zygosity Status of EE-GH7

3.1. Primers

Two primers recognizing the nucleotide sequences of the wild-type locus prior to insertion of the elite event, were designed in such a way that they are in a direction towards each other, and one primer is located in the region corresponding to the 5' or 3' flanking region of the event, and one primer is directed to the junction sequence of the target site deletion in the pre-insertion locus, and the 3' or 5' flanking region, respectively. A third primer is included which is targeted to the junction sequence of the foreign DNA in the transgenic locus, and the 3' or 5' flanking region, respectively. Presence of these three primers allows simultaneous PCR amplification of the EE-GH7 specific sequence as well as of the wild type sequence.

The following primers were found to give particularly clear and reproducible results in a zygosity scoring PCR reaction on EE-GH7 DNA:

PRIM0726:
(SEQ ID No.: 11)
5'-CAAACTCCgAATAgTTCCATCAATTT-3'

(target: Plant DNA of the 5' flanking sequence)

PRIM0733
(SEQ ID No.: 12)
5'-gAAggTCggAgTCAACggATTgCTTACTTAAgCATTgTTCTgTTTCA

-continued

Ag-3'

(target: 5'flanking target site deletion junction sequence (nt 22-49 of SEQ ID No. 12) extended with a 5' tail (nt 1-21 of SEQ ID No. 12)).

PRIM0731
(SEQ ID No.: 13)
5'-gAAggTgACCAAgTTCATgCTggCCCAgTACTgTTgTTCTgTTTC-3'

(target: 5'flanking foreign DNA junction sequence (nt 22-45 of SEQ ID No. 13) extended with a 5' tail (nt 1-21 of SEQ ID No. 13)).

3.2. Amplified Fragments

The expected amplified fragments in the PCR reaction are:
For primer pair PRIM0726-PRIM0733: 76 bp (wild-type locus)
For primer pair PRIM0726-PRIM0731: 71 bp (EE-GH7 locus)

3.3. Template DNA

Template DNA was prepared using the AGOWA sbeadex Maxi Plant Kit. When using DNA prepared with other methods, a test run utilizing different amounts of template should be done. Between 5 and 80 ng of genomic template DNA can be used.

3.4. Assigned Positive and Negative Controls

To avoid false positives or negatives, it is advisable that the following positive and negative controls should be included in a PCR run:
  Homozygous control: a genomic DNA sample containing the target sequence described homozygously
  Hemizygous control: a genomic DNA sample containing the target sequence described hemizygously
  Wild type control (DNA negative control): a genomic DNA sample not containing the target sequence described
  No Template Control (NTC): a water sample

3.5. PCR Conditions

Optimal results were obtained under the following conditions. Obviously, other Taq polymerases can be used, and then the conditions can differ to follow supplier recommendations.
  the PCR mix for 10 µl reactions contains:
    x µl template DNA (20 ng)
    5.0 µl KASPar v3.0 Reagent (96-384 well formulation) (LGC)
    0.14 µl assay mix
    water up to 25 µl
  100 µl assay mix contains:
    12 µl PRIM0731 (100 pmol/µl)
    12 µl PRIM0733 (100 pmol/µl)
    30 µl PRIM0726 (100 pmol/µl)
    water up to 100 µl
the KASPar v3.0 reagent contains a FRET cassette labelled with VIC dye corresponding to the tail of PRIM0733 (wild-type specific primer), and a FRET cassette labelled with FAM dye corresponding to the tail of PRIM0731 (EE-GH7 specific primer).

the thermocycling profile to be followed for optimal results is the following:

| | |
|---|---|
| | 15 min. at 94° C. |
| Followed by: | 20 sec. at 94° C. |
| | 1 min. at 65° C. (−0.8° C./cycle) |
| | For 10 cycles |
| Followed by: | 20 sec. at 94° C. |
| | 1 min. at 57° C. |
| | For 26 cycles |

3.6. Data Analysis

For all samples, fluorescent Signal to Background ratio's (S/B) are calculated for both the event specific and the wild type locus reactions. The background level is determined by the NTC samples.

Figure 5:
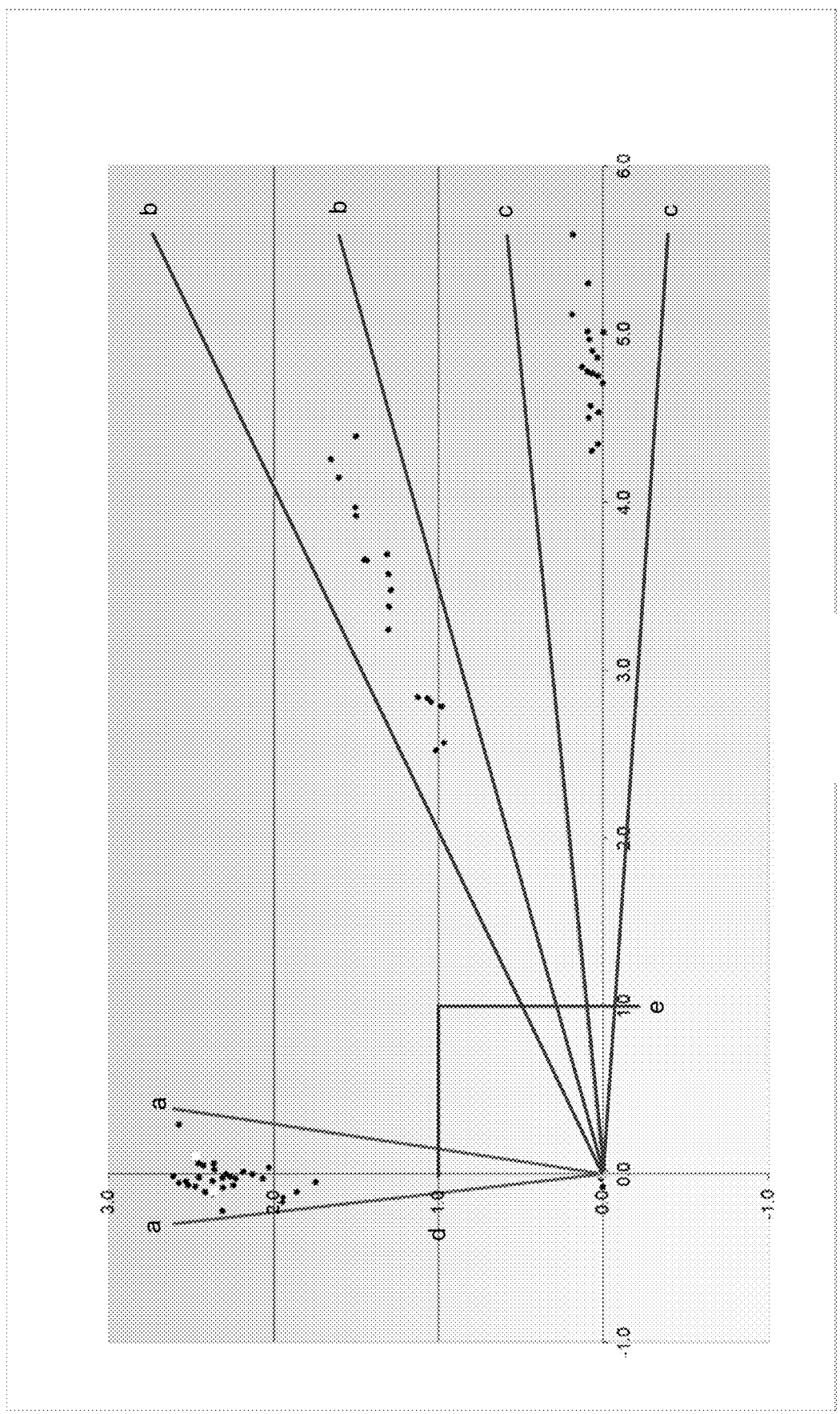
FIG. 5: Results obtained by the zygosity scoring PCR protocol developed for EE-GH7. Y-axis: Signal to background (S/B) VIC; X-axis: Signal to background (S/B) FAM. Black dots: samples. Lines "a" delineate wild-type samples; lines "b" delineate samples hemizygous for EE-GH7; lines "c" delineate samples homozygous for EE-GH7. "d": minimum S/B VIC; "e": minimum S/B FAM.

Results of test samples are only valid if the control samples give the expected results, ie:
  The homozygous control is scored "homozygous"
  The hemizygous control is scored "hemizygous"
  The wild type control is scored "wild type"
  The NTC's only show fluorescent background levels
A sample is scored:
  "Homozygous": if the sample is located in the homozygous cluster and the S/B exceeds the minimum acceptance S/B ratio (i.e. FAM S/B ratio)
  "Hemizygous": if the sample is located in the hemizygous cluster and the S/B exceeds the minimum acceptance S/B ratio (i.e. FAM and VIC S/B ratio)
  "Wild type": if the sample is located in the wild type cluster and the S/B exceeds the minimum acceptance S/B ratio (i.e. VIC S/B ratio)
  "Non-conclusive": if the sample is located in between the 3 clusters or if the S/B is lower than the minimum acceptance S/B ratio An example of S/B ratios for material from homozygous lines for EE-GH7, for material from lines hemizyous for EE-GH7, and for wild-type lines is shown in FIG. 5. It can be seen that only VIC, but no FAM is measured in wild-type material (located in the wild type cluster and the S/B exceeds the minimum acceptance S/B ratio), both VIC and FAM are measured in material hemizyous for EE-GH7 (located in the hemizygous cluster and the S/B exceeds the minimum acceptance S/B ratio), and only FAM is measured for material homozygous for EE-GH7 (located in the homozygous cluster and the S/B exceeds the minimum acceptance S/B ratio).

4. Introgression of EE-GH7 into Preferred Cultivars

Elite Event EE-GH7 was introduced by repeated backcrossing into cotton variety ST 457. Agronomic performance was determined for EE-GH7 in the ST 457 background and in the Coker 312 background in the field at four different locations. Plants were treated with 210 g IFT (2×) pre emergence, with 210 g IFT (2×) post emergence Early (E; 2-4 leaf stage), with 4244 g Roundup PowerMax (2×) post emergence Early (E; 2-4 leaf stage), Mid (M; between squaring and before bloom) and Late (L; Bloom), with 210 g IFT+4244 g Roundup PowerMax (2×) post emergence, or with 210 g IFT pre-emergence followed by 4244 g Roundup Powermax post emergence. Agronomic parameters were compared to the respective untreated plants with the same background but not comprising EE-GH7. For only one treatment, a significant difference in lint yield was observed between untreated control plants and plants comprising EE-GH7 (210 g IFT+4244 g Roundup PowerMax (2×) post emergence). This was however due to a difference observed at one location only; at the other four locations, there was no significant difference between untreated control plants and plants with the same genetic background but not comprising EE-GH7. For all other treatments, the lint yield in plants comprising EE-GH7 was not significantly different from the lint yield of the untreated control plants. This shows that in the Coker 312 background and in the ST 547 background, the lint yield of plants comprising EE-GH7 treated with different combinations of herbicides is highly equivalent to lint yield of untreated control plants not comprising the event.

Agronomic equivalency was tested by comparing different agronomic parameters for plants comprising EE-GH7 with null-segregants and with wild-type (not comprising EE-GH7) plants at four locations. In the ST 457 background, length, POB (percent open bolls), LP (lint percentage), SI (seed index) was not significantly different from both wild type and null segregants. Uniformity of plants comprising EE-GH7 in the ST 457 background was significantly higher than both wild type controls and null segregants, and lint yield was significantly higher than for the null segregant but not than the wild type. In the Coker 312 background, there was some fluctuation in performance, resulting in a slightly lower lint yield and lint percentage as compared to the wild type. This lower lint yield and lint percentage was however not observed as compared to the null segregant, indicating it was not due to the presence of the event. All other parameters in the Coker 312 background were not significantly different. In summary, these data show that the plants comprising EE-GH7 behave for different agronomic parameters very similar to isogenic plants not comprising EE-GH7.

Elite Event EE-GH7 was introduced by repeated backcrossing into cotton varieties 05M0201 and 11A, in which it was stacked with the events T304-40, comprising glufosinate tolerance and the Cry1Ab gene as described in WO2008/122406, GHB119 comprising glufosinate tolerance and the Cry2Ae gene as described in WO2008/151780, and COT102 comprising the VIP3A gene as described in WO2004/039986. Plants were treated with 105 g IFT (IX) pre-emergence, 210 g IFT (2×) pre emergence, with 105 g IFT (1×) post emergence, with 210 g IFT (2×) post emergence, with 4244 g Roundup PowerMax (2×) post emergence (E, M and L), with 210 g IFT pre-emergence followed by 4244 g Roundup PowerMax (2×) post emergence, with 1761 g Liberty (2×) post emergence (E and M), with 210 g IFT (2×) pre emergence followed by 1761 g Liberty (2×) post emergence (E and M), or with 210 g IFT (2×) pre-emergence and 1761 g Liberty (2×) post emergence. Agronomic parameters were compared to plants with the respective background but not comprising EE-GH7 across 8 locations. Only for one treatment and one parameter (lint length in the treatment with 210 g IFT pre-emergence followed by 4244 g Roundup PowerMax (2×) post emergence) lint length was significantly higher than of the control. Lint length was not significantly different between plants comprising EE-GH7 and the control plants for any of the other treatments. For all the other parameters tested (lint yield, micronaire, strength, and final plant height), and for all treatments, there was no significant difference between plants comprising EE-GH7 and the control plants. These data show that the plants comprising EE-GH7 behave, in different commercial backgrounds, for different agronomic parameters very similar to isogenic plants not comprising EE-GH7. Moreover, the presence of EE-GH7 does not impact the tolerance to glufosinate (Liberty) conferred by T304-40 and GHB119, nor does it affect the expression of the Bt genes (Cry1Ab, Cry2Ae, VIP3A).

Agronomic equivalency of plants comprising EE-GH7 in cotton varieties 05M0201m 11A, and 04SC095, all comprising T304-40, GHB119 and COT102 as described above, was tested by comparing different agronomic parameters for plants comprising EE-GH7 with null-segregants and with parent material for 05M0201, 11A and 04SC095 plants not comprising EE-GH7 at four locations. It was found that the plants comprising EE-GH7 perform similarly to null segregants in agronomic equivalency trials.

Elite event EE-GH7 is introduced by repeated backcrossing into commercial cotton cultivars such as but not limited to FM 989, FM 958, FM 966, FM 832, FM 5013, FM 5015, FM 5017, FM 958B, FM 832B, FM 989BR, FM 991BR, FM 800BR, FM 960BR, FM 5045BR, FM 960B2R, FM 989B2R, FM 991B2R, FM 800B2R, FM 958LL, FM 966LL, FM 993LL, FM 981LL, FM 832LL, FM 5035LL, FM 960B2, FM 955LLB2, FM 965LLB2, FM 988LLB2, FM 9063B2F, FM 9058F, FM 9060F, FM 9068F, AFD 5062LL, AFD 5065B2F, AFD 5064F, AFD 3070F, AFD 3074F, FM 1880B2F, FM 1600LL, FM 1800LL, FM 9150F, FM 820F, FM 840B2F, FM 835LLB2, FM 1735LLB2, FM 1740B2F, FM 9180B2F, FM 1640B2F, FM 1840B2F, FM 966B, FM 9160B2F, FM 1845LLB2, ST4288B2F, ST5288B2F, FM 1773LLB2, FM 9101GT, FM 9103GT, FM 9250GL, FM 9170B2F, FM 2011GT, FM 2989GLB2, ST 4145LLB2, FM 2484B2F, FM 1944GLB2, FM 8270GLB2, ST 5445LLB2, FM 1320GL, ST 4946GLB2, ST 4747GLB2, ST 6448GLB2, ST 5032GLT, FM 2322GL, FM 1830GLT, FM 2334GLT, ST 5289GLT, ST 6182GLT, ST 5115GLT, FM 1900GLT, FM 2007GLT, ST 4949GLT, ST 4848GLT, FM 1911GLT.

It is observed that the introgression of the elite event into these cultivars does not significantly influence any of the desirable phenotypic or agronomic characteristics of these cultivars (no linkage drag) while expression of the transgene, as determined by glyphosate and/or isoxaflutole tolerance, meets commercially acceptable levels. This confirms the status of event EE-GH7 as an elite event.

Elite event EE-GH7 may be advantageously combined with other elite events available in the market. Particularly useful transgenic plants which may be treated according to the invention are plants containing transformation events, or a combination of transformation events, and that are listed for example in the databases for various national or regional regulatory agencies including Event 531/PV-GHBK04 (cotton, insect control, described in WO 2002/040677), Event 1143-14A (cotton, insect control, not deposited, described in WO 06/128569); Event 1143-51B (cotton, insect control, not deposited, described in WO 06/128570); Event 1445 (cotton, herbicide tolerance, not deposited, described in US-A 2002-120964 or WO 02/034946), Event 281-24-236 (cotton, insect control—herbicide tolerance, deposited as PTA-6233, described in WO 05/103266 or US-A 2005-216969); Event 3006-210-23 (cotton, insect control—herbicide tolerance, deposited as PTA-6233, described in US-A 2007-143876 or WO 05/103266); Event CE43-67B (cotton, insect control, deposited as DSM ACC2724, described in US-A 2009-217423 or WO 06/128573); Event CE44-69D (cotton, insect control, not deposited, described in US-A 2010-0024077); Event CE44-69D (cotton, insect control, not deposited, described in WO 06/128571); Event CE46-02A (cotton, insect control, not deposited, described in WO 06/128572); Event COT102 (cotton, insect control, not deposited, described in US-A 2006-130175 or WO 04/039986); Event COT202 (cotton, insect control, not deposited, described in US-A 2007-067868 or WO 05/054479); Event COT203 (cotton, insect control, not deposited, described in WO 05/054480); Event GHB119 (cotton, insect control—herbicide tolerance, deposited as ATCC PTA-8398, described in WO 08/151780); Event GHB614 (cotton, herbicide tolerance, deposited as ATCC PTA-6878, described in US-A 2010-050282 or WO 07/017186); Event LLcotton25 (cotton, herbicide tolerance, deposited as ATCC PTA-3343, described in WO 03/013224 or US-A 2003-097687); Event MON15985 (cotton, insect control, deposited as ATCC PTA-2516, described in US-A 2004-250317 or WO 02/100163); Event MON88913 (cotton, herbicide tolerance, deposited as ATCC PTA-4854, described in WO 04/072235 or US-A 2006-059590); Event MON88701 (cotton, herbicide tolerance, deposited as PTA-11754, described in WO 2012/134808), Event T304-40 (cotton, insect control—herbicide tolerance, deposited as ATCC PTA-8171, described in US-A 2010-077501 or WO 08/122406); Event T342-142 (cotton, insect control, not deposited, described in WO 06/128568); event MON88701 (cotton, ATCC Accession No PTA-11754, WO 2012/134808A1), event pDAB4468.18.07.1 (cotton, herbicide tolerance, ATCC Accession No PTA-12456), WO2013112525A2, event pDAB4468.19.10.3 (cotton, herbicide tolerance, ATCC Accession No PTA-12457), WO2013112527A1, event A26-5 (Cotton, insect control) WO2013170398, event A2-6 (Cotton, insect control) WO2013170399, event A26-5 (Cotton, as described in WO2013170398A1), event A2-6 (Cotton, as described in WO2013170399A1).

Particularly useful to the invention are plants combining EE-GH7 with Event GHB119 (cotton, insect control—herbicide tolerance, deposited as ATCC PTA-8398, described in WO 08/151780), Event T304-40 (cotton, insect control—herbicide tolerance, deposited as ATCC PTA-8171, described in US-A 2010-077501 or WO 08/122406), and Event COT102 (cotton, insect control, not deposited, described in US-A 2006-130175 or WO 04/039986).

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event EE-GH7 was deposited at the ATCC (10801 University Blvd., Manassas, Va. 20110-2209) on 24 Feb. 2016, under ATCC accession number PTA-122856, and the viability thereof was confirmed. Alternative names for EE-GH7 are event GHB 811.

The above description of the invention is intended to be illustrative and not limiting.

Various changes or modifications in the embodiments described may occur to those skilled in the art. These can be made without departing from the spirit or scope of the invention.

The invention claimed is:

1. A nucleic acid molecule comprising the nucleotide sequence of SEQ ID No. 1 from nucleotide 1207 to nucleotide 1228, or of SEQ ID No. 1 from nucleotide 8022 to nucleotide 8043, or the complement of said sequences, reference seed comprising said nucleic acid molecule having been deposited at the ATCC under deposit number PTA-122856.

2. A cotton plant, cell, part, tissue, seed or progeny thereof, comprising elite event EE-GH7 in its genome, reference seed comprising said event having been deposited at the ATCC under deposit number PTA-122856.

3. Cotton genomic DNA obtainable from the cotton plant, cell part, tissue, seed or progeny thereof of claim 2, said cotton genomic DNA comprising elite event EE-GH7.

4. A seed comprising elite event EE-GH7 deposited at the ATCC under deposit number PTA-122856 or derivatives therefrom, said derivatives comprising elite event EE-GH7.

5. A transgenic cotton plant comprising elite event EE-GH7 in its genome, reference seed comprising said event having been deposited at the ATCC under deposit number PTA-122856, which is tolerant to isoxaflutole and/or glyphosate.

6. The cotton plant, cell, part, tissue, seed or progeny thereof according to claim 2, further comprising event T304-40, comprising glufosinate tolerance and the Cry1Ab gene;
event GHB119 comprising glufosinate tolerance and the Cry2Ae gene; and/or
event COT102 comprising the VIP3A gene.

7. A method for producing a cotton plant or seed comprising elite event EE-GH7, comprising crossing a plant according to claim 2 with another cotton plant, and planting the seed obtained from said cross.

8. A cotton product produced from the cotton plant, cell, part, tissue, seed or progeny thereof of claim 2, wherein the cotton product comprises cotton genomic DNA comprising elite event EE-GH7.

9. A method for weed control, comprising treating a field in which the cotton seeds of claim 2 are sown with an HPPD inhibitor herbicide, before the cotton plants emerge but after the seeds are sown.

10. A method of weed control, comprising treating the cotton plants of claim 2 with an HPPD inhibitor herbicide after the cotton plants emerge.

11. A method for protecting the emerging cotton plants of claim 2 from competition by weeds, comprising treating a field to be planted with said cotton plants with an HPPD inhibitor herbicide, before the cotton plants are planted or the seeds are sown, followed by planting or sowing of said cotton plants or seeds in said pre-treated field.

12. The method according to claim 9, further comprising treating the cotton plants with glyphosate.

13. A method for weed control, comprising treating the cotton plants of claim 2 with glyphosate after the cotton plants emerge.

14. A method for identifying elite event EE-GH7 in biological samples, reference seed comprising said event having been deposited at the ATCC under deposit number PTA-122856, which method comprises detection of an EE-GH7 specific region with a specific primer pair which specifically recognizes the 5' or 3' flanking region of the foreign DNA comprising herbicide tolerance genes in EE-GH7, and part of the foreign DNA contiguous with said 5' or 3' flanking region.

15. A primer pair comprising a first and a second labeled primer, said first primer recognizing the 5' flanking region of the foreign DNA comprising herbicide tolerance genes in EE-GH7, reference seed comprising said event having been deposited at the ATCC under deposit number PTA-122856, said 5' flanking region comprising the nucleotide sequence of SEQ ID No. 1 from nucleotide 1217, or said first primer recognizing the 3' flanking region of the foreign DNA comprising the herbicide tolerance genes in EE-GH7, said 3' flanking region comprising the nucleotide sequence of the complement of SEQ ID No. 1 from nucleotide 8033 to nucleotide 9328, and said second primer recognizing a sequence within the foreign DNA comprising the nucleotide sequence of SEQ ID No. 1 from nucleotide 1218 to nucleotide 8032 or the complement thereof.

16. A specific probe for identifying elite event EE-GH7, reference seed comprising said event having been deposited at the ATCC under deposit number PTA-122856, in biological samples, said specific probe comprising part of the 5' flanking sequence or the 3' flanking sequence of EE-GH7 and the sequence of the foreign DNA contiguous therewith, wherein the probe specifically recognizes the nucleotide sequence of SEQ ID NO. 1 from nucleotide 1207 to nucleotide 1228 or of SEQ ID NO. 1 from nucleotide 8022 to nucleotide 8043.

17. A method for determining the zygosity status of a plant, plant material or seed comprising elite event EE-GH7, reference seed comprising said event having been deposited at the ATCC under deposit number PTA-122856, said method comprising amplifying DNA fragments of between 50 and 1000 bp from a nucleic acid present in said biological samples using a polymerase chain reaction with at least three primers, two of said primers specifically recognizing pre-insertion plant DNA, and the third of said primers recognizing a sequence within the foreign DNA.

18. A method of detecting the presence of elite event EE-GH7, reference seed comprising said event having been deposited at the ATCC under deposit number PTA-122856, in biological samples through hybridization with a complementary labeled nucleic acid probe in which the probe:target nucleic acid ratio is amplified through recycling of the target nucleic acid sequence, said method comprising:
 a) hybridizing said target nucleic acid sequence to a first nucleic acid oligonucleotide comprising the nucleotide sequence of SEQ ID No. 1 from nucleotide 1218 to nucleotide 1235 or its complement or said first nucleic acid oligonucleotide comprising the nucleotide sequence of SEQ ID No. 1 from nucleotide 8015 to 8032 or its complement;
 b) hybridizing said target nucleic acid sequence to a second nucleic acid oligonucleotide comprising the nucleotide sequence of SEQ ID No. 1 from nucleotide 1200 to nucleotide 1217 or its complement or said labeled nucleic acid probe comprising the nucleotide sequence of SEQ ID No. 1 from nucleotide 8033 to nucleotide 8050 or its complement, wherein said first and second oligonucleotide overlap by at least one nucleotide and wherein either said first or said second oligonucleotide is labeled to be said labeled nucleic acid probe;
 c) cleaving only the labeled probe within the probe:target nucleic acid sequence duplex with an enzyme which causes selective probe cleavage resulting in duplex disassociation, leaving the target sequence intact;
 d) recycling of the target nucleic acid sequence by repeating steps (a) to (c); and
 e) detecting cleaved labeled probe, thereby determining the presence of said target nucleic acid sequence.

19. The method according to claim 17, wherein the two primers which specifically recognizing pre-insertion plant DNA are a primer comprising the nucleotide sequence of SEQ ID No. 11 and a primer comprising the nucleotide sequence of SEQ ID No. 12, and wherein the third of said primers comprises the nucleotide sequence of SEQ ID No. 13.

20. A method for identifying elite event EE-GH7 in biological samples, reference seed comprising said event having been deposited at the ATCC under deposit number PTA-122856, which method comprises detection of an EE-GH7 specific region with a specific probe, said specific probe comprising part of the 5' flanking sequence or the 3' flanking sequence of EE-GH7 and the sequence of the foreign DNA contiguous therewith, wherein the probe specifically recognizes the nucleotide sequence of SEQ ID NO. 1 from nucleotide 1207 to nucleotide 1228 or of SEQ ID NO. 1 from nucleotide 8022 to nucleotide 8043.

* * * * *

SEQUENCE LISTING

```
<160> NUMBER OF SEQ ID NOS: 13

<210> SEQ ID NO 1
<211> LENGTH: 9328
<212> TYPE: DNA
<213> ORGANISM: Artificial
<220> FEATURE:
<223> OTHER INFORMATION: Sequence of the EE-GH7 transgenic locus
<220> FEATURE:
<221> NAME/KEY: misc_feature
<222> LOCATION: (1)..(1217)
<223> OTHER INFORMATION: 5' flanking sequence
<220> FEATURE:
<221> NAME/KEY: misc_feature
<222> LOCATION: (1218)..(1219)
<223> OTHER INFORMATION: RB (partial): partial right border region of
      the T-DNA of Agrobacterium tumefaciens
<220> FEATURE:
<221> NAME/KEY: misc_feature
<222> LOCATION: (1218)..(8032)
<223> OTHER INFORMATION: Foreign DNA
<220> FEATURE:
<221> NAME/KEY: terminator
<222> LOCATION: (1277)..(1943)
<223> OTHER INFORMATION: ThistonAt: histone terminator from Arabidopsis
      - complement
<220> FEATURE:
<221> NAME/KEY: misc_feature
<222> LOCATION: (1960)..(3036)
<223> OTHER INFORMATION: hppdPf W336: mutated coding sequence of hppd -
      complement
<220> FEATURE:
<221> NAME/KEY: transit_peptide
<222> LOCATION: (3037)..(3408)
<223> OTHER INFORMATION: TPotp Y-1Pa: transit peptide - complement
<220> FEATURE:
<221> NAME/KEY: promoter
<222> LOCATION: (3417)..(3929)
<223> OTHER INFORMATION: Pcsvmv: promotor of the casein vein mosaic
      virus  - complement
<220> FEATURE:
<221> NAME/KEY: promoter
<222> LOCATION: (4028)..(4944)
<223> OTHER INFORMATION: Ph4a748: histone promoter from Arabidopsis
<220> FEATURE:
```

```
<221> NAME/KEY: Intron
<222> LOCATION: (4984)..(5449)
<223> OTHER INFORMATION: Intron1 h3At: first intron of gene II of
      histone H3
<220> FEATURE:
<221> NAME/KEY: transit_peptide
<222> LOCATION: (5463)..(5834)
<223> OTHER INFORMATION: TPotpC: optimized transit peptide
<220> FEATURE:
<221> NAME/KEY: misc_feature
<222> LOCATION: (5835)..(7172)
<223> OTHER INFORMATION: 2mepsps: double mutated EPSPsynhtase from corn
<220> FEATURE:
<221> NAME/KEY: terminator
<222> LOCATION: (7193)..(7859)
<223> OTHER INFORMATION: ThistonAt: histone terminator from Arabidopsis
<220> FEATURE:
<221> NAME/KEY: misc_feature
<222> LOCATION: (8026)..(8032)
<223> OTHER INFORMATION: LB (partial): partial left border region of the
      T-DNA of Agrobacterium tumefaciens
<220> FEATURE:
<221> NAME/KEY: misc_feature
<222> LOCATION: (8033)..(9328)
<223> OTHER INFORMATION: 3' flanking sequence

<400> SEQUENCE: 1
ttcctaattc tatcgtgcac atgtgatgca ttccttttt tataacaagg aagttccaat      60
ttcatatctc caacgtagta tcatttagca taaaataaaa gctagctaaa acttagcagt     120
tttggtcatt tccatttaga tatatatatt ttcaaaggtc tatatttatc tgtttgtatt    180
aataaaaacc atccattaaa tggttgtaac gaattaacca aaggaatcta aaacagtaaa    240 aaaaagttt acctccatta gtcagaagct gtttactccc ctttcaagtc gtttcatcaa     300
attaagaggt tacatcaaca aatagggtga attttttac tgttagtgac ttcctctttt     360 tttttttgg tatcaggatg ttgaatacat tttttgtcag ttactttcta aaatgataaa     420
taatttatca cgaaaaaacg tataagtcaa atattaatat atatttttta aaattattaa    480
taaaaaatat aaatatcaaa tactcataaa taaattttta tttacaattg aattaaaatc    540
tgattgaaac tcaaacaaat gcagcaaaaa gtttgaaata atagtatagg gatacgtaaa    600
agttataaaa caaatacata aaatgtaaat atatggttt ggattggat ttgaatttgg      660 atttggattt gggaatattt cttttcatgc ggctggtgtc taatcgtgag atttttctgac   720 ttgacggcta ccattatttt tccatccgca ttatcttctt tattgtactc aaaatatttc    780
ttatttgaaa atgaatttct tataaaatag taaactaaca ttcggattt taagccaata    840 tcaatgttct attacattgg aggaacatgg gtcatgactc atgagcacca atacacaatt    900
gtggtgtaca tattgagccg tgtgacatat gcataaaatt ttactcattc tccgttaata    960
tcacactttt atcggtgtat ataaatttta ttatttaat ttattttaa atttataatc    1020 atattaaaaa taaaaatat taaattaagt atttttttag agatattaaa attaaaaata   1080
gttttaaaat ttatatttat atacaaatgt gtttataatt gaaatctata tgacgtgcac    1140
ataattatta ttatcaaact ccgaatagtt ccatcaattt tatcatttat gtatttggaa    1200
gccttgaaac agaacaacag tactgggccc cctcgagggc gatcgctacg tacctgcagg   1260
cccgggttaa ttaaggcccg atcaaatctg agggacgtta aagcgatgat aaattggaac    1320
cagaatatag aatctttgtt ctgctctagc ttttcttctg tacatttttt acgattagac    1380
tatgattttc attcaataac caaaattctg aagtttgtca tcaagttgct caatcaaact   1440
tgtaccggtt tgtttcggtt ttatatcagc tcactgttac actttaacca aaatcggttt   1500
atgtcttaat aaaggaattg agtcggttta actcatatcc gtaccaatgc gacgtcgtgt   1560
```

```
ccgcgtttca gtagctttgc tcattgtctt ctacgggaac tttcccggac ataggaaccg    1620 cccctttcgtt atcctcatcc atcgtgaaat caggaaataa atgttcgaag atttgaggtc    1680
aaaagtcgaa tttcatgttg tctcttctat ttagatacaa aattgaagca attttcacca    1740
atttaatgcc aaaatttaaa acaacgctga taaagtgaaa cttgattcga tttatatttc    1800
aaccgaaact gctgaagcaa gaagaaaaag cgtaattaca cataacaaga acgctaccgc    1860
aaactactaa acgccaaacc caatacaaaa gtaaaacgca gacgcttaag tgagaaaccc    1920
agaaaacaca aacgcggatc gggcgacgcg tgctagcttt taatcagcgg tcaaaacccc    1980
tctacgaact tgatccctct ctatcgattc gaaaagtgct ttgaagttcc attctccgaa    2040
gccatcgtcc cctttacgct gaatgaactc aaagaaaacg ggtcccatga gagtctcgga    2100
aaagatttgt aacaggagcc tcttatcacc ctcaaccgaa gaaccatcga gaagtatacc    2160
cctggcttgc agttggtcca cgggttcccc atgatcaggc aggcgtcctt ctagcatctc    2220
atagtaagta tcgggaggtg cagtcatgaa tctcatacct atcttcttca atgcatccca    2280
ggttttcaca agatcatcag tcagaaaagc gacatgctga atgccttcac cattgaactg    2340
cataagaaac tcttcgattt gtcctgcacc tttgcttgac tcttcgttga gtggaatcct    2400
tatcatacca tctggagcgc tcatagcctt tgatgtgaga ccagtatact ctcctttgat    2460
gtcaaagtat ctagcttccc taaagttgaa gagtttctca tagaagttag cccagtatac    2520
cattcgtcca cgatagacgt tgtgtgtcaa atgatcaata accttcaagc cagcaccgac    2580
aggatttcgt tccacgcctt caagatagac gaaatctatg tcgtagatag aactgccctc    2640
tccgaatctg tcgataagat acaacggtgc accaccgatg cctttgatgg ctggaagatt    2700
caattccata ggtccagtgt caatgtgaat aggctgagct ccaagttcta atgccctatt    2760
gtaggctttc tgggaatcct taactcgaaa tgccatgcca caaacggatg gtccatgttc    2820
ggcagcaaag tagcttgcta tagagttagg ttcgttgttc aagatcaggt taatctctcc    2880
ttgccgatat aggtgcacgt tcttactgcg atgtgtagct accttagtaa accccataat    2940
ctcaaagatg ggttcaaggg tcccaggtgt aggagaagca aactcaatga actcgaaacc    3000
catgagtccc ataggattct cgtatagatc agccatgcat ctaatcctac ctccgttgct    3060
aacattcccc agcgatctgg aagatctccg agcaactggc aaactagcag tactcttcaa    3120
cccttgaaat ggtgccacag ctgtggcaga gctggccatc atcacagtgg gagccataga    3180
tagcggaggt aagtaggata aggtctcaaa cttcttgttg ccataggctg ccagacttg    3240 catatactgt actctcccac cgttgctcgg aagtgttgag aagtcattag ccttcttagt    3300
ggttggaaat gcagcatttg acttaagacc tgtgaacgga gccaccatat tagcttgggc    3360
tggtgcggta cgtgaaacag tggcaactga agatgaaata ctagccatgg ttttggacaa    3420
acttacaaat ttctctgaag ttgtatcctc agtacttcaa agaaatagc ttacaccaaa    3480 ttttttcttg tttcacaaa tgccgaactt ggttccttat ataggaaaac tcaagggcaa    3540
aaatgacacg gaaaaatata aaaggataag tagtgggga taagattcct ttgtgataag    3600
gttactttcc gcccttacat tttccacctt acatgtgtcc tctatgtctc tttcacaatc    3660
accgacctta tcttcttctt ttcattgttg tcgtcagtgc ttacgtcttc aagattcttt    3720
tcttcgcctg gttcttcttt ttcaatttct acgtattctt cttcgtattc tggcagtata    3780
ggatcttgta tctgtacatt cttcatttt gaacataggt tgcatatgtg ccgcatattg    3840
atctgcttct tgctgagctc acataatact tccatagttt ttcccgtaaa cattggattc    3900
```

```
ttgatgctac atcttggata attaccttcg cggccgcttg gcgcgccgaa ttcgatatca    3960
ttaccctgtt atccctaaag cttattaata taacttcgta tagcatacat tatacgaagt    4020
tatgtttgtc gaggagaaat atgagtcgag gcatggatac actaagttcc cctgaagtga    4080
gcatgatctt tgatgctgag atgattccca gagcaagata gtttgtgctg caagtgacac    4140
aattgtaatg aaaccaccac tcaacgaatt tacttgtggc tttgacatgt cgtgtgctct    4200
gtttgtattt gtgagtgccg gttggtaatt attttttgtta atgtgatttt aaaacctctt    4260
atgtaaatag ttactttatc tattgaagtg tgttcttgtg gtctatagtt tctcaaaggg    4320
aaattaaaat gttgacatcc catttacaat tgataacttg gtatacacaa actttgtaaa    4380
tttggtgata tttatggtcg aaagaaggca atacccattg tatgttccaa tatcaatatc    4440
aatacgataa cttgataata ctaacatatg attgtcattg tttttccagt atcaatatac    4500
attaagctac tacaaaatta gtataaatca ctatattata aatcttttc ggttgtaact    4560
tgtaattcgt gggttttaa ataaaagca tgtgaaaatt ttcaaataat gtgatggcgc    4620
aattttattt tccgagttcc aaaatattgc cgcttcatta ccctaatttg tggcgccaca    4680
tgtaaaacaa aagacgattc ttagtggcta tcactgccat cacgcggatc actaatatga    4740
accgtcgatt aaaacagatc gacggtttat acatcatttt attgtacaca cggatcgata    4800
tctcagccgt tagatttaat atgcgatctg attgctcaaa aaatagactc tccgtctttg    4860
cctataaaaa caatttcaca tctttctcac ccaaatctac tcttaaccgt tcttcttctt    4920
ctacagacat caatttctct cgactctaga ggatccaagc ttatcgattt cgaacccctc    4980
aggcgaagaa caggtatgat tgtttgtaa ttagatcagg ggtttaggtc tttccattac    5040
tttttaatgt ttttctgtt actgtctccg cgatctgatt ttacgacaat agagtttcgg    5100
gttttgtccc attccagttt gaaaataaag gtccgtcttt taagtttgct ggatcgataa    5160
acctgtgaag attgagtcta gtcgatttat tggatgatcc attcttcatc gttttttct    5220
tgcttcgaag ttctgtataa ccagattgt ctgtgtgcga ttgtcattac ctagccgtgt    5280
atcgagaact agggttttcg agtcaatttt gccccttttg gttatatctg gttcgataac    5340
gattcatctg gattagggtt ttaagtggtg acgtttagta ttccaatttc ttcaaaattt    5400
agttatggat aatgaaaatc cccaattgac tgttcaattt cttgttaaat gcgcagatca    5460
caatggcttc gatctcctcc tcagtcgcga ccgttagccg gaccgcccct gctcaggcca    5520
acatggtggc tccgttcacc ggccttaagt ccaacgccgc cttccccacc accaagaagg    5580
ctaacgactt ctccacccct cccagcaacg gtggaagagt tcaatgtatg caggtgtggc    5640
cggcctacgg caacaagaag ttcgagacgc tgtcgtacct gccgccgctg tctatggcgc    5700
ccaccgtgat gatggcctcg tcggccaccg ccgtcgctcc gttccagggg ctcaagtcca    5760
ccgccagcct ccccgtcgcc cgccgctcct ccagaagcct cggcaacgtc agcaacggcg    5820
gaaggatccg gtgcatggcc ggcgccgagg agatcgtgct gcagcccatc aaggagatct    5880
ccggcaccgt caagctgccg gggtccaagt cgctttccaa ccggatcctc ctactcgccg    5940
ccctgtccga ggggacaaca gtggttgata acctgctgaa cagtgaggat gtccactaca    6000
tgctcggggc cttgaggact cttggtctct ctgtcgaagc ggacaaagct gccaaaagag    6060
ctgtagttgt tggctgtggt ggaaagttcc cagttgagga tgctaaagag gaagtgcagc    6120
tcttcttggg gaatgctgga atcgcaatgc ggtccttgac agcagctgtt actgctgctg    6180
gtggaaatgc aacttacgtg cttgatggag taccaagaat gagggagaga cccattggcg    6240
acttggttgt cggattgaag cagcttggtg cagatgttga ttgtttcctt ggcactgact    6300
```

```
gcccacctgt tcgtgtcaat ggaatcggag ggctacctgg tggcaaggtc aagctgtctg    6360
gctccatcag cagtcagtac ttgagtgcct tgctgatggc tgctcctttg gctcttgggg    6420
atgtggagat tgaaatcatt gataaattaa tctccattcc gtacgtcgaa atgacattga    6480
gattgatgga gcgttttggt gtgaaagcag agcattctga tagctgggac agattctaca    6540
ttaagggagg tcaaaaatac aagtcccctg aaaatgccta tgttgaaggt gatgcctcaa    6600
gcgcaagcta tttcttggct ggtgctgcaa ttactggagg actgtgact gtggaaggtt     6660 gtggcaccac cagtttgcag ggtgatgtga agtttgctga ggtactggag atgatgggag    6720
cgaaggttac atggaccgag actagcgtaa ctgttactgg cccaccgcgg gagccatttg    6780
ggaggaaaca cctcaaggcg attgatgtca acatgaacaa gatgcctgat gtcgccatga    6840
ctcttgctgt ggttgccctc tttgccgatg gcccgacagc catcagagac gtggcttcct    6900
ggagagtaaa ggagaccgag aggatggttg cgatccggac ggagctaacc aagctgggag    6960
catctgttga ggaagggccg gactactgca tcatcacgcc gccggagaag ctgaacgtga    7020
cggcgatcga cacgtacgac gaccacagga tggcgatggc tttctccctt gccgcctgtg    7080
ccgaggtccc cgtcaccatc cgggaccctg ggtgcacccg gaagaccttc cccgactact    7140
tcgatgtgct gagcactttc gtcaagaatt aagctctaga actagtggat cccccgatcc    7200
gcgtttgtgt tttctgggtt tctcacttaa gcgtctgcgt tttacttttg tattgggttt    7260
ggcgtttagt agtttgcggt agcgttcttg ttatgtgtaa ttacgctttt tcttcttgct    7320
tcagcagttt cggttgaaat ataaatcgaa tcaagtttca ctttatcagc gttgttttaa    7380
attttggcat taaattggtg aaaattgctt caattttgta tctaaataga agagacaaca    7440
tgaaattcga cttttgacct caaatcttcg aacatttatt tcctgatttc acgatggatg    7500
aggataacga aagggcggtt cctatgtccg ggaaagttcc cgtagaagac aatgagcaaa    7560
gctactgaaa cgcggacacg acgtcgcatt ggtacggata tgagttaaac cgactcaatt    7620
cctttattaa gacataaacc gattttggtt aaagtgtaac agtgagctga tataaaaccg    7680
aaacaaaccg gtacaagttt gattgagcaa cttgatgaca aacttcagaa ttttggttat    7740
tgaatgaaaa tcatagtcta atcgtaaaaa atgtacagaa gaaaagctag agcagaacaa    7800
agattctata ttctggttcc aatttatcat cgctttaacg tccctcagat ttgatcggga    7860
aacataactt cgtatagcat acattatacg aagttatcaa acgtcgtga acagtttgg     7920 ttaactataa cggtcctaag gtagcgatcg aggcattacg gcattacggc actcgcgagg    7980
gtccgaatct atgtcgggtg cggagaaaga ggtaatgaaa tggcaattta caatagaaga    8040
tagaattgat gcaatcagtt ttagaataaa acgatatgt cgatcgtgta aattttgaaa     8100
atattgactg aatggtttcg attaaaccta actttcaagt tcaatcata agatgtttat     8160 cccctaaaag attcctagtt gctaagagtt tacaaaatag agctatccat tcgaattaga    8220
cttattcaaa tagtttaaat tagtggtcta atgtcgaagg tatgctcgaa agttttgaag    8280
aaaaatatta aatttaaaaa ttgagttttg tacaaaaatt taattatttt tttatttaaa    8340
taagatttga gctcaaattt caatatttaa agtccgagct ttactcaatt tagtctagta    8400
cgctcttaaa ggtataacat aatttaatct attttatata tatgaaaaat ggaaatcgac    8460
agatccatga ttatttatta ctaaggaccc catttaagtt cccaggacaa tgaagggaca    8520
tcaactatta ataaataaat ggaatggtaa gtgtcatcag catagtgcgc atctagacaa    8580
gctcttgacg atatataaat gtatatgtca cttaacaacc gtgcaaacct tatctgatta    8640
```

```
aaccaaggca aaacgcccaa ccagattaat taagggcat atatagcaca gatcagacgt    8700
gaccagtcag ggattagggg gtgagctcac ctcaccacaa atgcctttca ttttggctcg    8760
acaatcttta taatctgtcc atgcaaaagg atgcattcca ggtcaataaa atgtagtcac    8820
tgagttgtag agatcaaacc atttgtctcc aagaacatac atgagtggac tttgagcctc    8880
aaactttgtt atatttgtgt ggttaggtat aaataataat cttcctcact cttctcaatt    8940
atttggcaac tgtagaaata attgccaaaa agctttgaaa gttttgtcaa ttttgttaca    9000
ttgtgtcaat tcacctttg aaggtgcaag aacttgtctc aaaattgagt ctttacatat    9060
atattataat gatttctgaa agttttaac atgagcagta caagtattat tggtactaat    9120
tactcataat tttgtttttg ttttgtggt gaaaatggtc gtgaaagagg ctttctttta    9180
agaatcaaga tttgagaaag tattcttttg ttttgttttg ttttattggc aaaccaatga    9240
ttagatatgt taatagaatt taacttatag acacgtttag gacataactt ttaacattgt    9300
ccttaaaaag ttttaaaagt ctaattaa                                     9328
```

<210> SEQ ID NO 2
<211> LENGTH: 2526
<212> TYPE: DNA
<213> ORGANISM: Artificial
<220> FEATURE:
<223> OTHER INFORMATION: EE-GH7 insertion locus
<220> FEATURE:
<221> NAME/KEY: misc_feature
<222> LOCATION: (1)..(1217)
<223> OTHER INFORMATION: 5' flanking sequence
<220> FEATURE:
<221> NAME/KEY: misc_feature
<222> LOCATION: (1218)..(1230)
<223> OTHER INFORMATION: TSD: Target site deletion
<220> FEATURE:
<221> NAME/KEY: misc_feature
<222> LOCATION: (1231)..(2526)
<223> OTHER INFORMATION: 3' flanking sequence

<400> SEQUENCE: 2

```
ttcctaattc tatcgtgcac atgtgatgca ttccttttt tataacaagg aagttccaat      60
ttcatatctc caacgtagta tcatttagca taaaataaaa gctagctaaa acttagcagt     120
tttggtcatt tccatttaga tatatatatt ttcaaaggtc tatatttatc tgtttgtatt    180
aataaaaacc atccattaaa tggttgtaac gaattaacca aaggaatcta aaacagtaaa    240
aaaaagtttt acctccatta gtcagaagct gtttactccc ctttcaagtc gtttcatcaa    300
attaagaggt tacatcaaca aatagggtga atttttttac tgttagtgac ttcctctttt    360
ttttttttgg tatcaggatg ttgaatacat tttttgtcag ttactttcta aaatgataaa    420
taatttatca cgaaaaaacg tataagtcaa atattaatat atatttttta aaattattaa    480
taaaaaatat aaatatcaaa tactcataaa taaattttta tttacaattg aattaaaatc    540
tgattgaaac tcaaacaaat gcagcaaaaa gtttgaaata atagtatagg gatacgtaaa    600
agttataaaa caaatacata aaatgtaaat atatggtttt ggatttggat ttgaatttgg    660
atttggattt gggaatattt cttttcatgc ggctggtgtc taatcgtgag attttctgac    720
ttgacggcta ccattatttt tccatccgca ttatcttctt tattgtactc aaaatatttc    780
ttatttgaaa atgaatttct tataaaatag taaactaaca ttcggatttt taagccaata    840
tcaatgttct attacattgg aggaacatgg gtcatgactc atgagcacca atacacaatt    900
gtggtgtaca tattgagccg tgtgacatat gcataaaatt ttactcattc tccgttaata    960
tcacactttt atcggtgtat ataaattta ttattttaat ttatttttaa atttataatc    1020
```

```
atattaaaaa taaaaaatat taaattaagt attttttag agatattaaa attaaaaata      1080
gttttaaaat ttatatttat atacaaatgt gtttataatt gaaatctata tgacgtgcac      1140
ataattatta ttatcaaact ccgaatagtt ccatcaattt tatcatttat gtatttggaa      1200
gccttgaaac agaacaatgc ttaagtaagc atagaagata gaattgatgc aatcagtttt      1260
agaataaaaa cgatatgtcg atcgtgtaaa ttttgaaaat attgactgaa tggtttcgat      1320
taaacctaac tttcaagttt caatcataag atgtttatcc cctaaaagat tcctagttgc      1380
taagagttta caaaatagag ctatccattc gaattagact tattcaaata gtttaaatta      1440
gtggtctaat gtcgaaggta tgctcgaaag ttttgaagaa aaatattaaa tttaaaaatt      1500
gagttttgta caaaaattta attattttt tatttaaata agatttgagc tcaaatttca      1560
atatttaaag tccgagcttt actcaattta gtctagtacg ctcttaaagg tataacataa      1620
tttaatctat tttatatata tgaaaaatgg aaatcgacag atccatgatt atttattact      1680
aaggacccca tttaagttcc caggacaatg aagggacatc aactattaat aaataaatgg      1740
aatggtaagt gtcatcagca tagtgcgcat ctagacaagc tcttgacgat atataaatgt      1800
atatgtcact taacaaccgt gcaaaaccta tctgattaaa ccaaggcaaa acgcccaacc      1860
agattaatta agggggcatat atagcacaga tcagacgtga ccagtcaggg attagggggt      1920
gagctcacct caccacaaat gcctttcatt ttggctcgac aatctttata atctgtccat      1980
gcaaaaggat gcattccagg tcaataaaat gtagtcactg agttgtagag atcaaaccat      2040
ttgtctccaa gaacatacat gagtggactt tgagcctcaa actttgttat atttgtgtgg      2100
ttaggtataa ataataatct tcctcactct tctcaattat ttggcaactg tagaaataat      2160
tgccaaaaag ctttgaaagt tttgtcaatt ttgttacatt gtgtcaattc accttttgaa      2220
ggtgcaagaa cttgtctcaa aattgagtct ttacatatat attataatga tttctgaaag      2280
tttttaacat gagcagtaca agtattattg gtactaatta ctcataattt tgttttttgtt      2340 tttgtggtga aaatggtcgt gaaagaggct ttcttttaag aatcaagatt tgagaaagta      2400
ttcttttgtt ttgttttgtt ttattggcaa accaatgatt agatatgtta atagaattta      2460
acttatagac acgtttagga cataactttt aacattgtcc ttaaaaagtt ttaaaagtct      2520
aattaa                                                                 2526
```

<210> SEQ ID NO 3
<211> LENGTH: 27
<212> TYPE: DNA
<213> ORGANISM: Artificial
<220> FEATURE:
<223> OTHER INFORMATION: primer PRIM0728

<400> SEQUENCE: 3
ctccgaatag ttccatcaat tttatca                                           27

<210> SEQ ID NO 4
<211> LENGTH: 21
<212> TYPE: DNA
<213> ORGANISM: Artificial
<220> FEATURE:
<223> OTHER INFORMATION: Primer PRIM0643

<400> SEQUENCE: 4
tgatcgggcc ttaattaacc c                                                 21

<210> SEQ ID NO 5

```
<211> LENGTH: 30
<212> TYPE: DNA
<213> ORGANISM: artificial
<220> FEATURE:
<223> OTHER INFORMATION: primer PRIM0638

<400> SEQUENCE: 5
cgaatagttc catcaattttt atcatttatg                              30

<210> SEQ ID NO 6
<211> LENGTH: 19
<212> TYPE: DNA
<213> ORGANISM: artificial
<220> FEATURE:
<223> OTHER INFORMATION: primer PRIM0639

<400> SEQUENCE: 6
tcgggcctta attaacccg                                           19

<210> SEQ ID NO 7
<211> LENGTH: 18
<212> TYPE: DNA
<213> ORGANISM: artificial
<220> FEATURE:
<223> OTHER INFORMATION: probe TM1576

<400> SEQUENCE: 7
agaacaacag tactgggc                                            18

<210> SEQ ID NO 8
<211> LENGTH: 23
<212> TYPE: DNA
<213> ORGANISM: artificial
<220> FEATURE:
<223> OTHER INFORMATION: Primer KVM157

<400> SEQUENCE: 8
cacatgactt agcccatctt tgc                                      23

<210> SEQ ID NO 9
<211> LENGTH: 21
<212> TYPE: DNA
<213> ORGANISM: artificial
<220> FEATURE:
<223> OTHER INFORMATION: Primer KVM158

<400> SEQUENCE: 9
cccacccttt tttggtttag c                                        21

<210> SEQ ID NO 10
<211> LENGTH: 26
<212> TYPE: DNA
<213> ORGANISM: artificial
<220> FEATURE:
<223> OTHER INFORMATION: Primer TM1304

<400> SEQUENCE: 10
tgcaggtttt ggtgccactg tgaatg                                   26

<210> SEQ ID NO 11
<211> LENGTH: 26
<212> TYPE: DNA
<213> ORGANISM: artificial
<220> FEATURE:
<223> OTHER INFORMATION: Primer PRIM0726

<400> SEQUENCE: 11
```

```
caaactccga atagttccat caattt                                                26

<210> SEQ ID NO 12
<211> LENGTH: 49
<212> TYPE: DNA
<213> ORGANISM: artificial
<220> FEATURE:
<223> OTHER INFORMATION: Primer PRIM0733

<400> SEQUENCE: 12
gaaggtcgga gtcaacggat tgcttactta agcattgttc tgtttcaag                       49

<210> SEQ ID NO 13
<211> LENGTH: 45
<212> TYPE: DNA
<213> ORGANISM: artificial
<220> FEATURE:
<223> OTHER INFORMATION: Primer PRIM0731

<400> SEQUENCE: 13
gaaggtgacc aagttcatgc tggcccagta ctgttgttct gtttc                           45
```